US008268808B2

(12) United States Patent
Trudsoe

(10) Patent No.: US 8,268,808 B2
(45) Date of Patent: Sep. 18, 2012

(54) CARRAGEENAN AND CARRAGEENAN-CONTAINING PRODUCTS

(75) Inventor: Jens Eskil Trudsoe, Roskilde (DK)

(73) Assignee: CP Kelco U.S., Inc., Atlanta, GA (US)

( * ) Notice: Subject to any disclaimer, the term of this patent is extended or adjusted under 35 U.S.C. 154(b) by 1412 days.

(21) Appl. No.: 11/767,648

(22) Filed: Jun. 25, 2007

(65) Prior Publication Data

US 2008/0317683 A1 Dec. 25, 2008

(51) Int. Cl.
*A01N 43/00* (2006.01)
*A61K 31/33* (2006.01)
*A23L 1/05* (2006.01)

(52) U.S. Cl. ........................................ 514/183; 426/575

(58) Field of Classification Search .................. None
See application file for complete search history.

(56) References Cited

U.S. PATENT DOCUMENTS

| 742,124 | A | 10/1903 | Martin et al. |
| 2,011,594 | A | 8/1935 | Seltzer et al. |
| 2,516,023 | A | 7/1950 | Siehrs et al. |
| 3,094,517 | A | 6/1963 | Stanley |
| 3,907,770 | A | 9/1975 | Strong |
| 3,956,173 | A | 5/1976 | Towle |
| 4,414,236 | A | 11/1983 | Moran et al. |
| 5,002,934 | A | 3/1991 | Norton et al. |
| 5,502,179 | A | 3/1996 | Larsen |
| 5,741,482 | A | 4/1998 | Modi |
| 5,801,240 | A | 9/1998 | Rideout et al. |
| 6,063,915 | A | 5/2000 | Hansen et al. |
| 2002/0098553 | A1 | 7/2002 | Bost et al. |
| 2004/0063927 | A1 | 4/2004 | Tsai et al. |
| 2004/0129174 | A1 | 7/2004 | Li et al. |
| 2005/0020828 | A1 | 1/2005 | Therkelsen |
| 2005/0106233 | A1 | 5/2005 | Andersen et al. |
| 2005/0171083 | A1 | 8/2005 | Magnusson et al. |
| 2007/0281065 | A1 | 12/2007 | Modliszewski et al. |

FOREIGN PATENT DOCUMENTS

| EP | 0355908 | | 2/1990 |
| EP | 0465373 | A2 | 8/1992 |

OTHER PUBLICATIONS

U.S. Statutory Invention Registration H2050 (Santos et al.) Oct. 1, 2002.
International Search Report Dated Sep. 2, 2008 for International Application No. PCT/US08/67610.
Disclosure Under 37 C.F.R. 1.56 dated Nov. 30, 2010, filed for U.S. Appl. No. 11/767,648.
International Search Report, Written Opinion, and International Preliminary Report on Patentability (PCT/US08/067610), International Searching Authority.
International Search Report, Written Opinion, and International Preliminary Report on Patentability (PCT/US08/066832), International Searching Authority.
International Search Report, Written Opinion, and International Preliminary Report on Patentability (PCT/US08/067261), International Searching Authority.
Disclosure Under 37 C.F.R. 1.56 dated Jan. 6, 2011 filed for U.S. Appl. No. 11/767,648.
Written Opinion and International Preliminary Report on Patentability, PCT/US2009/037047, International Searching Authority, Sep. 14, 2010.
Disclosure Under 37 CFR 1.56, dated Aug. 4, 2011, for U.S. Appl. No. 11/767,648.

*Primary Examiner* — Jeffrey S. Lundgren
*Assistant Examiner* — William Lee
(74) *Attorney, Agent, or Firm* — Sutherland Asbill & Brennan LLP

(57) ABSTRACT

The present invention discloses a carrageenan composition comprising: sodium in the range of about 5.410 to about 8.230%, preferably about 6.300 to about 8.230%, and more preferably about 7.380 to about 8.230%; potassium in the range of about 0.023% to about 0.248%, preferably about 0.023 to about 0.238%, and more preferably about 0.023 to about 0.078%; calcium in the range of 0.046-0.553%, preferably 0.046-0.446%, and more preferably 0.046-0.325%; and magnesium in the range of about 0.051 to about 0.338%, preferably about 0.051 to about 0.244% and more preferably about 0.051 to about 0.127%; wherein the carrageenan product has a gelling temperature of 7-30° C., preferably 7-18° C., more preferably 7-12° C.; and a melting temperature in the range 16-38° C., preferably 16-28° C., more preferably 16-24° C.

19 Claims, 22 Drawing Sheets

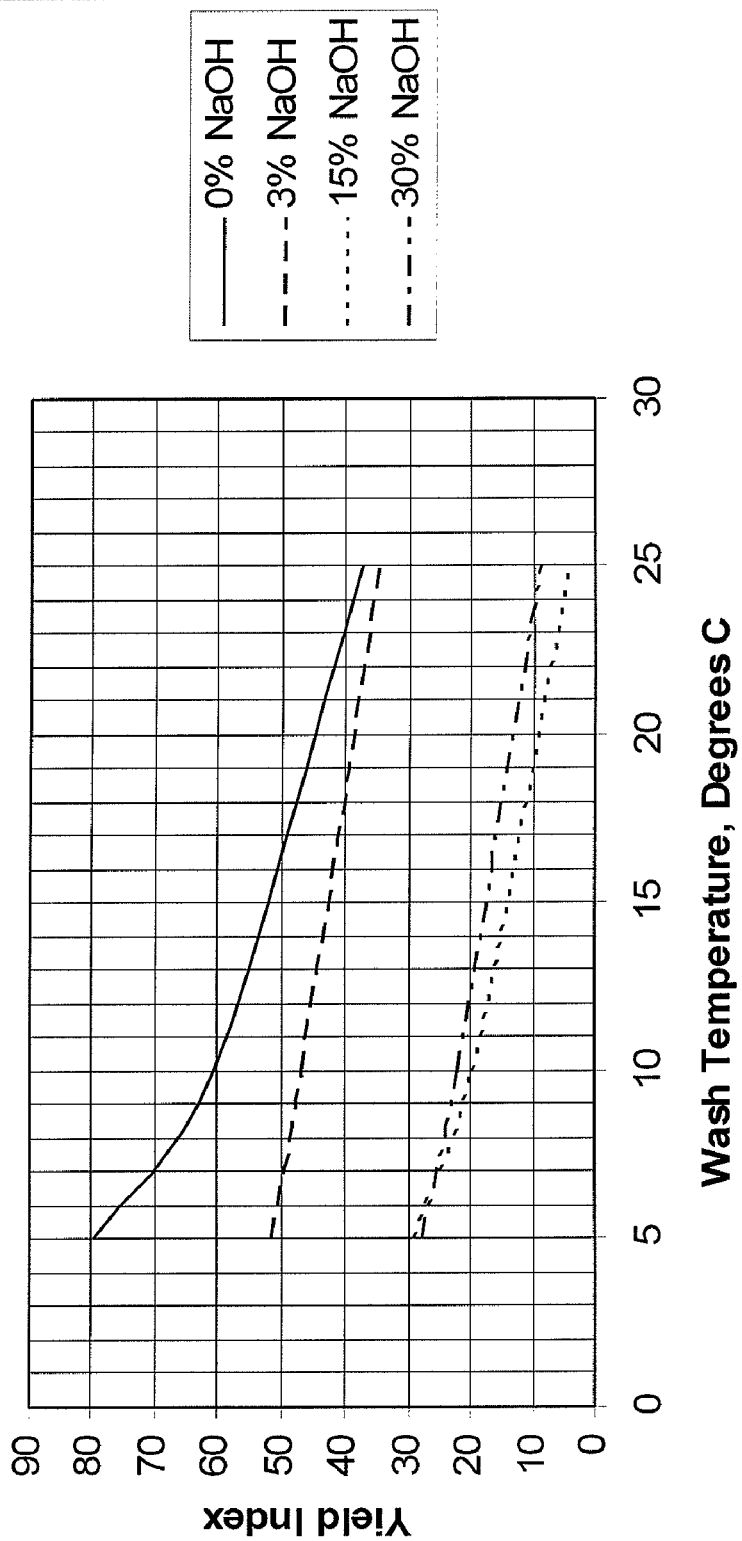
Fig. 1: Effect of washing temperature on yield index.

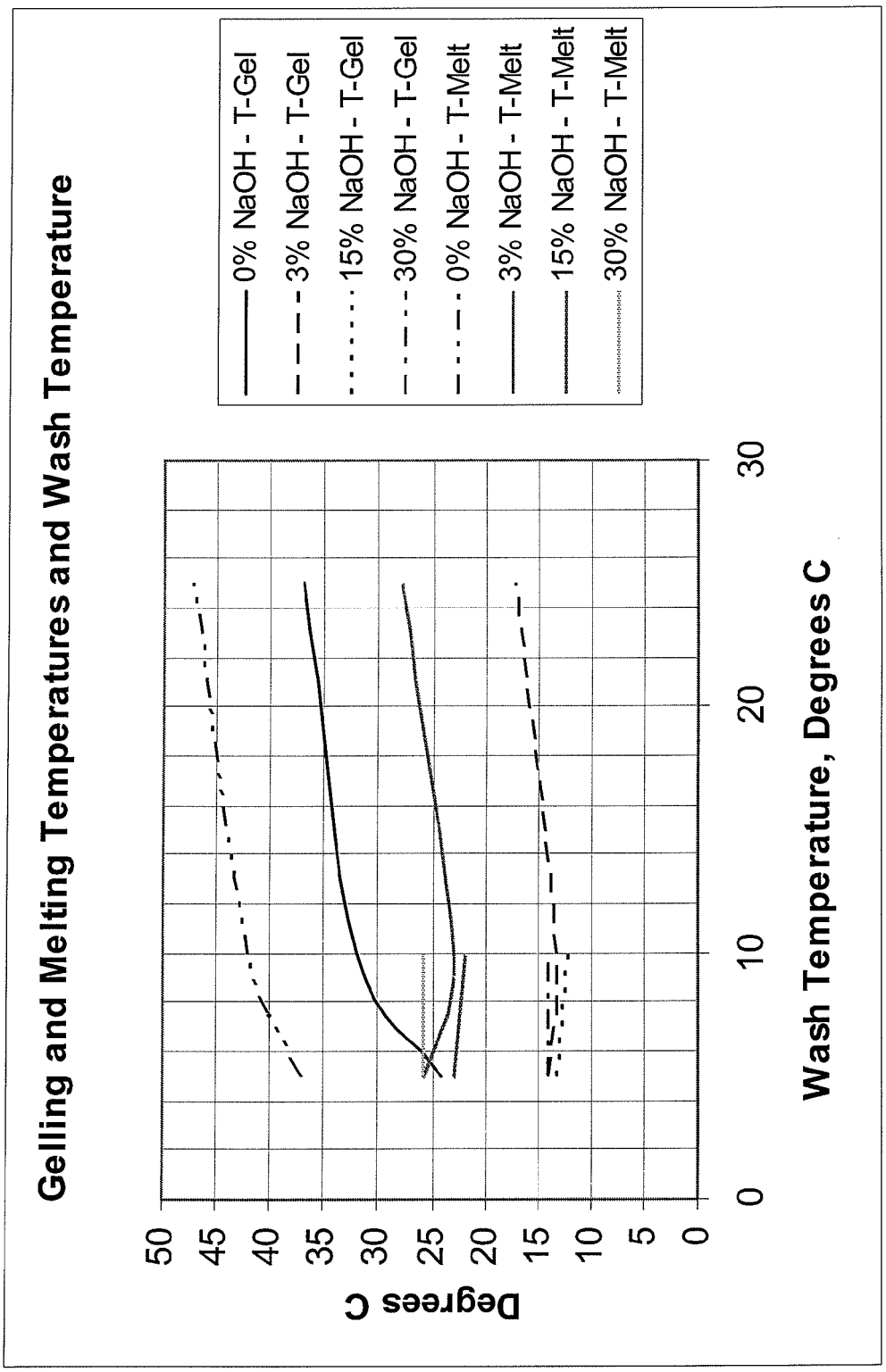
Fig. 2: Effect of wash temperature on gelling and melting temperature.

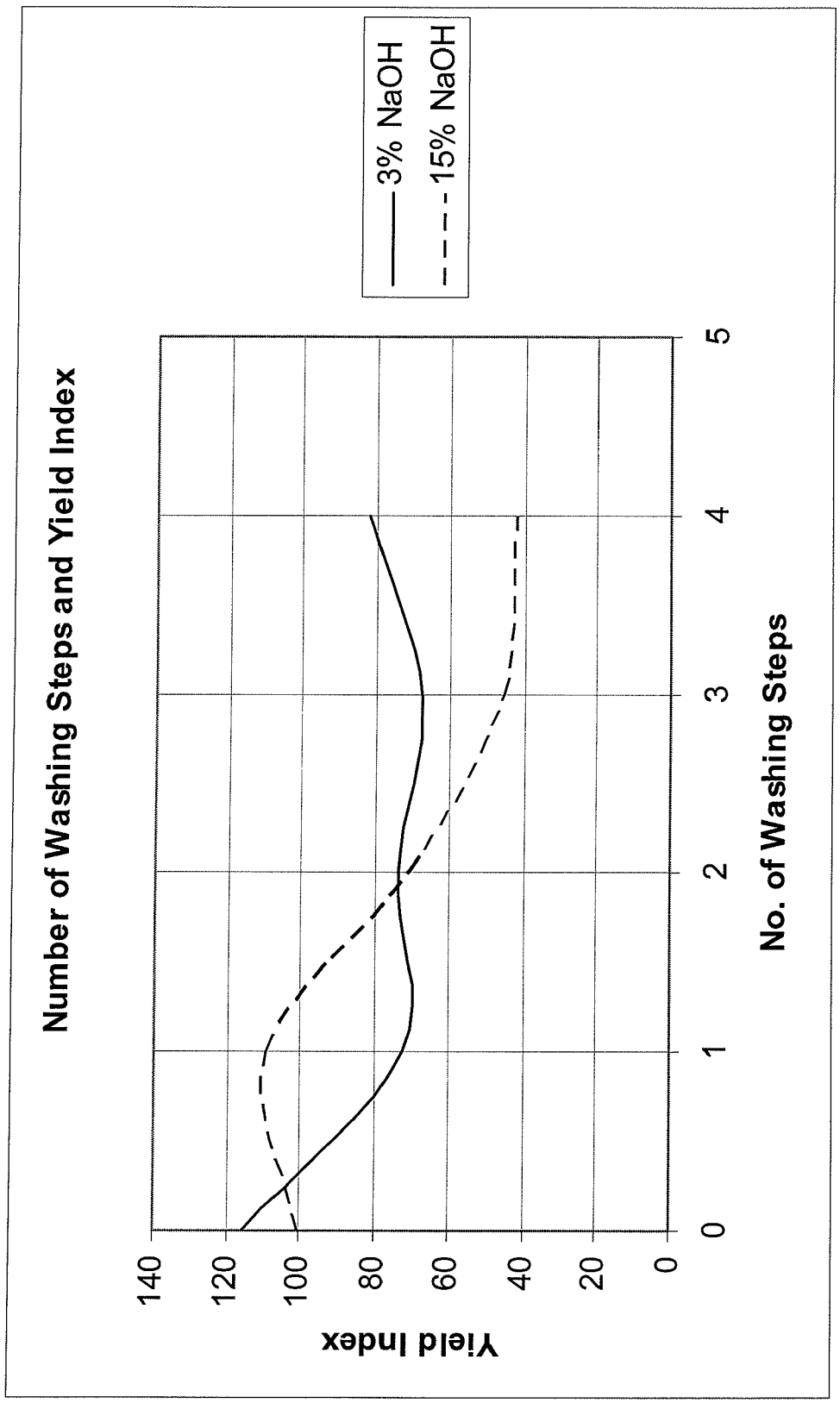
Fig. 3: Effect of number of washing steps on yield index.

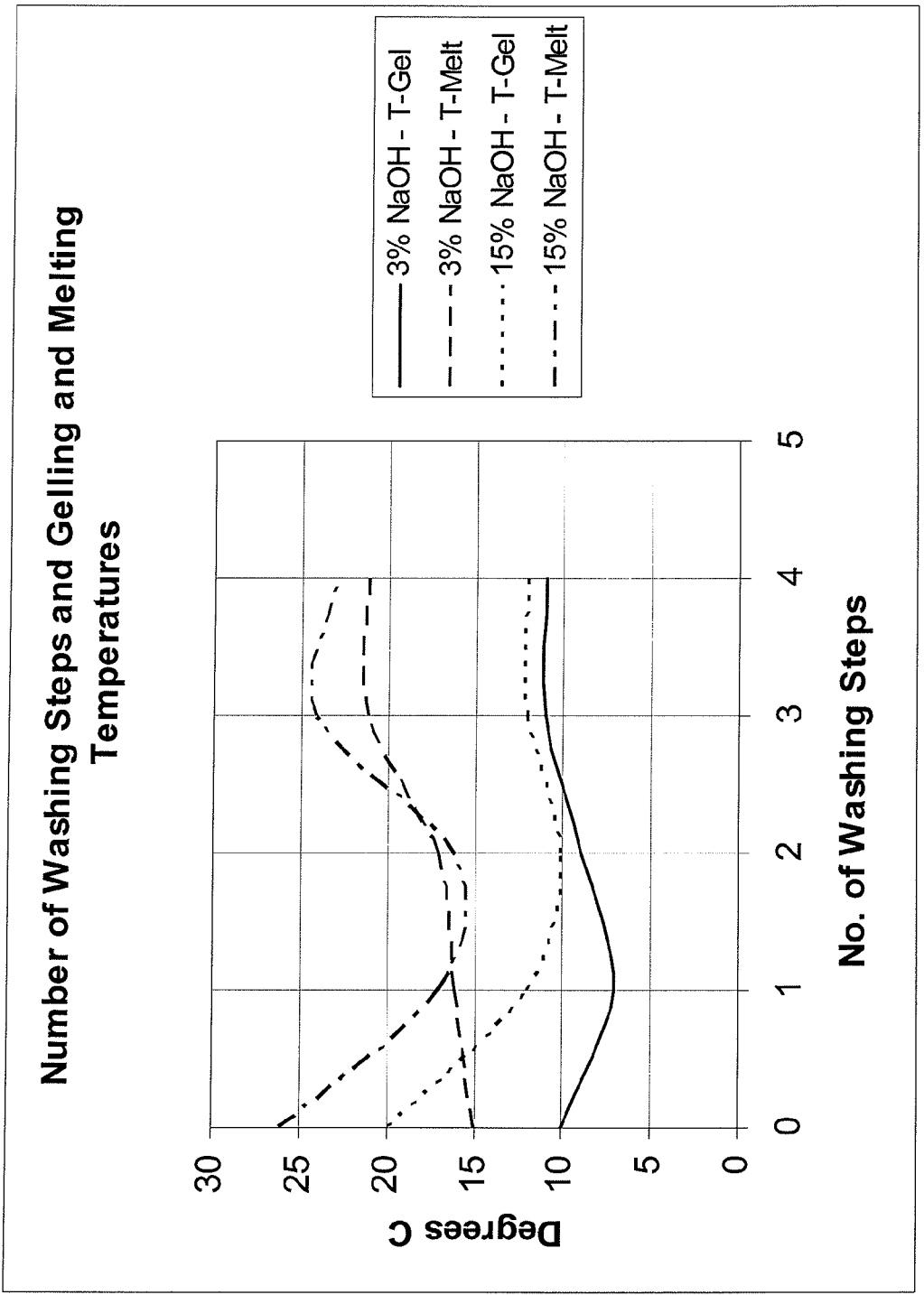
Fig. 4: Effect of number of washing steps on gelling and melting temperatures.

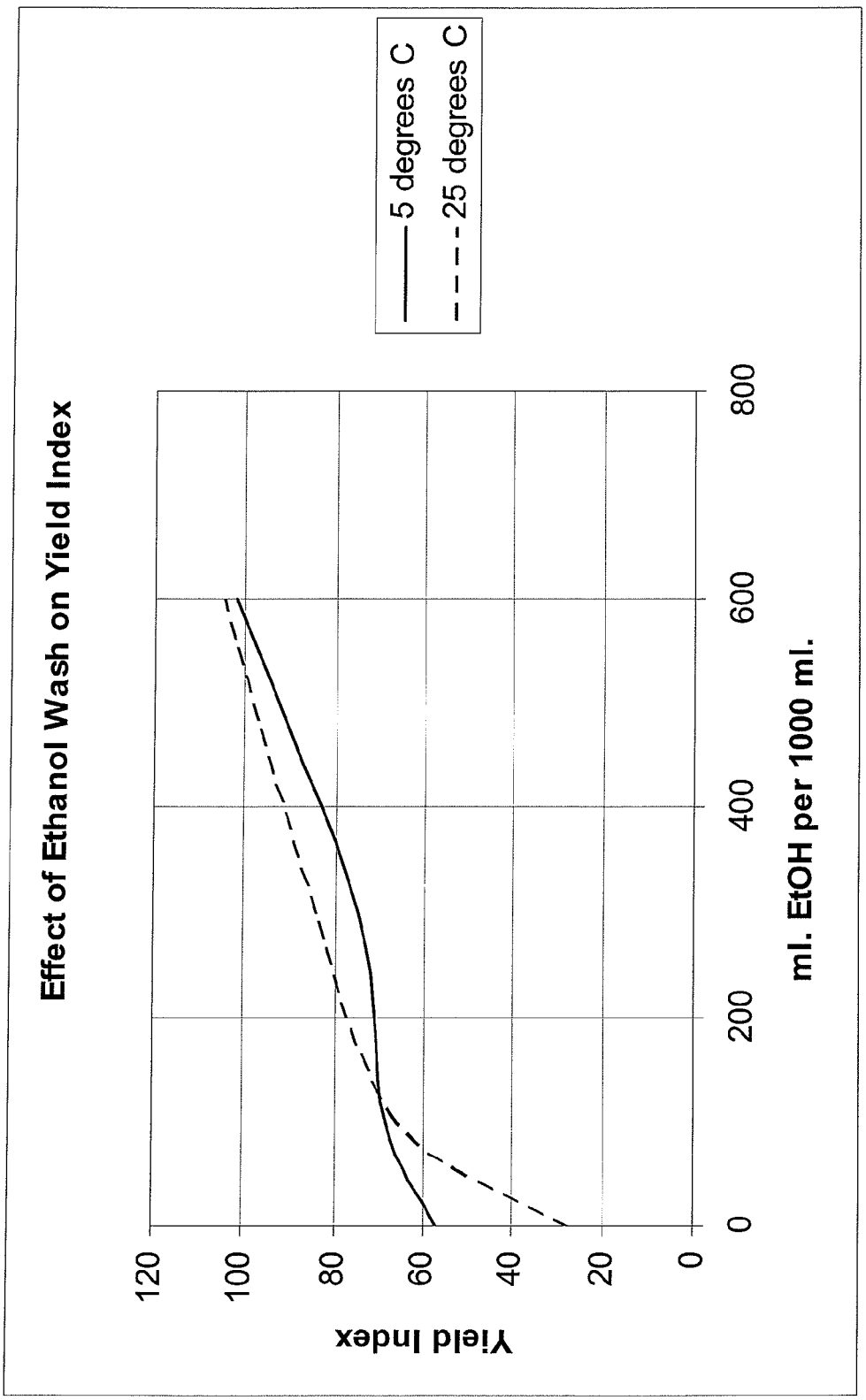
Fig. 5: Effect of ethanol concentration during washing on yield index.

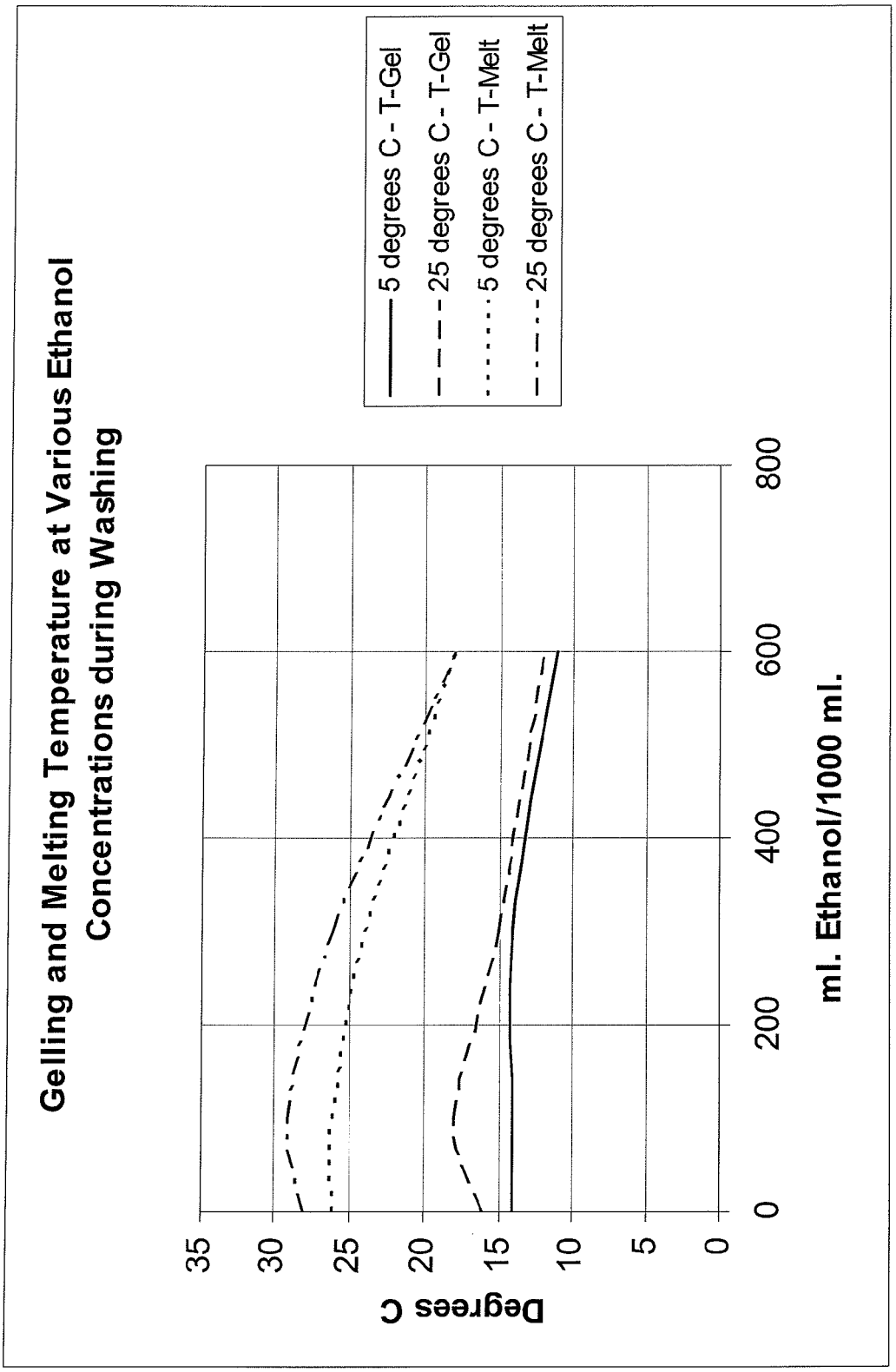
Fig. 6: Effect of ethanol concentration during washing on gelling and melting temperatures.

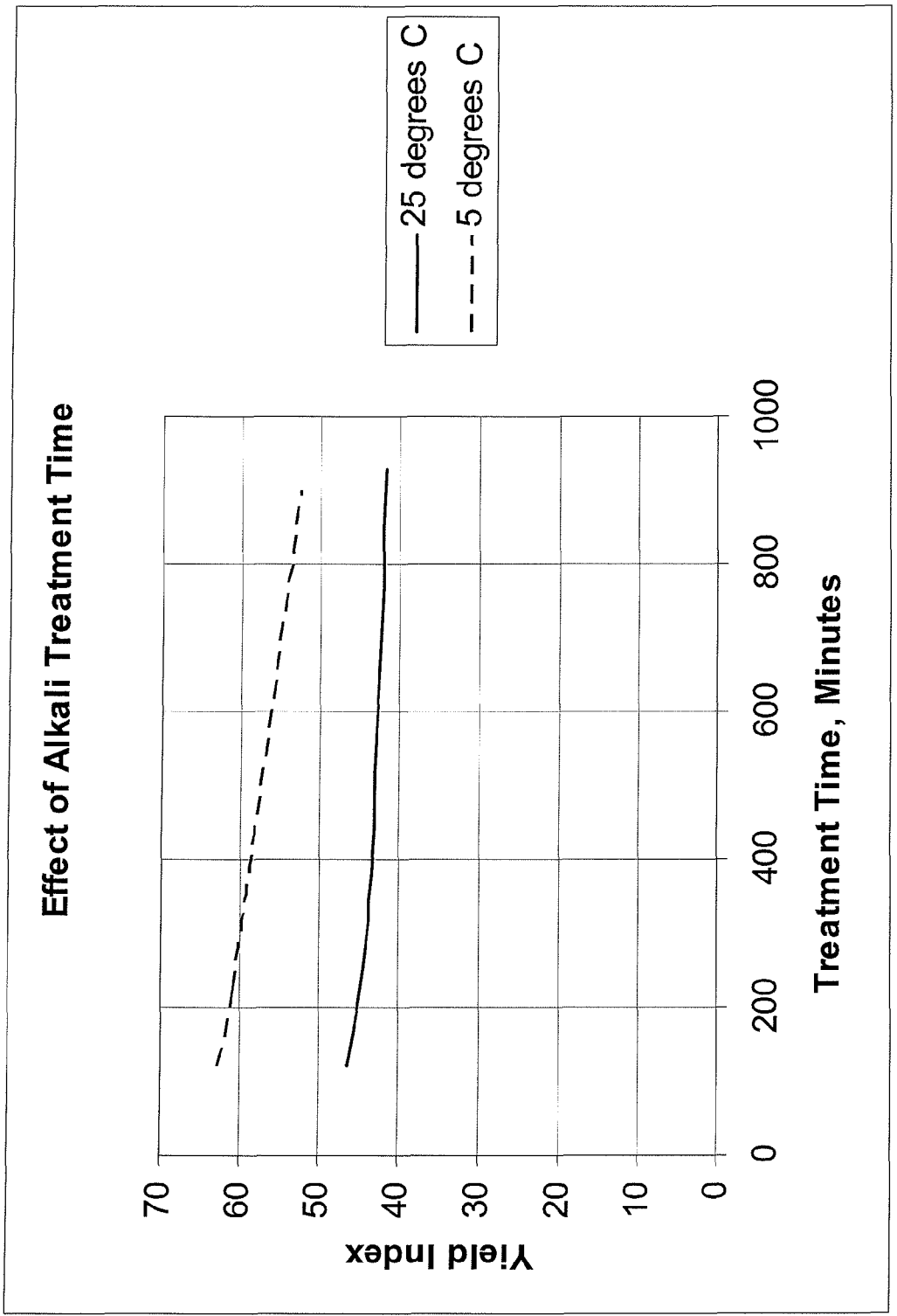
Fig. 7: Effect of alkali treatment time on yield index.

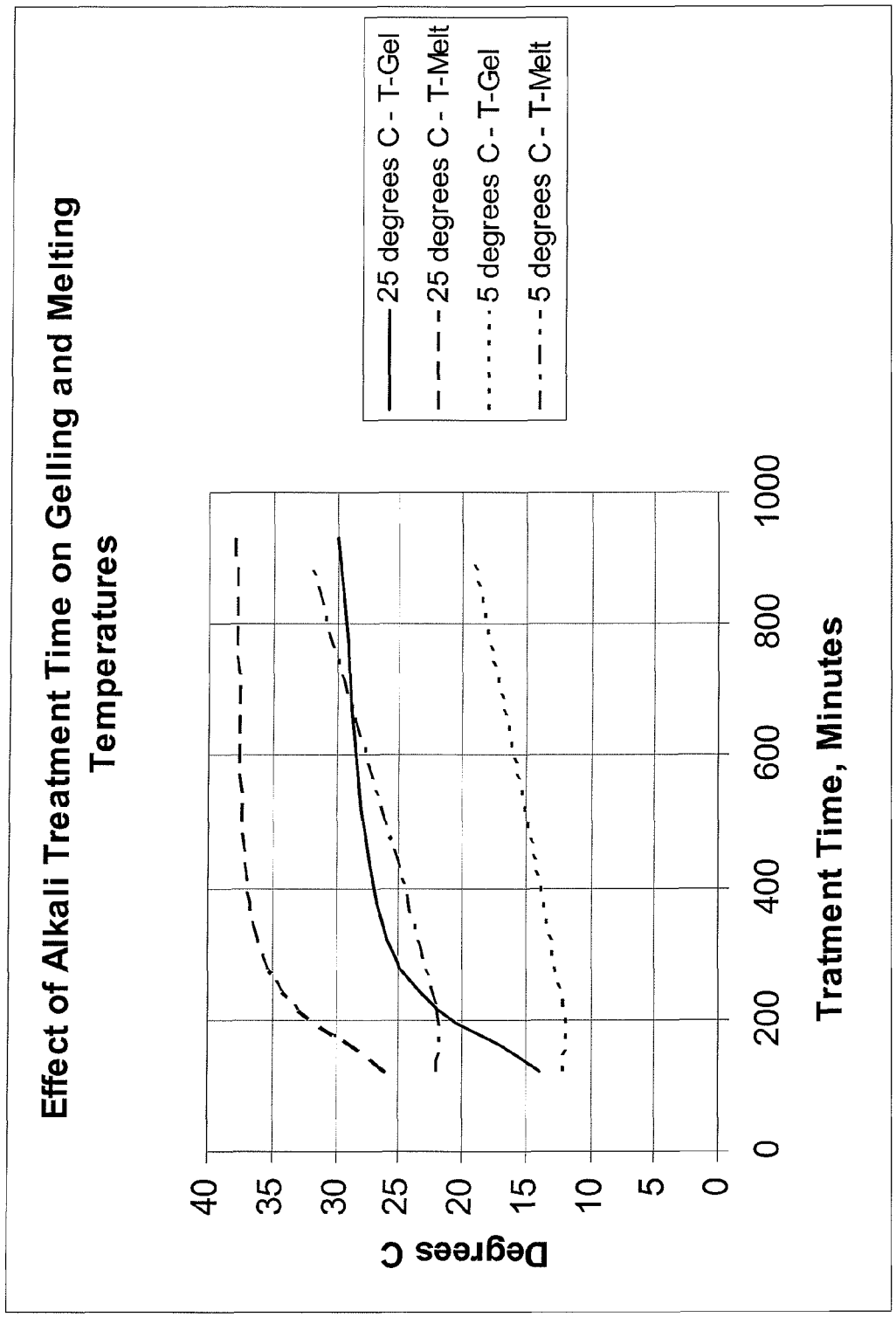
Fig. 8: Effect of alkali treatment time on gelling and melting temperatures.

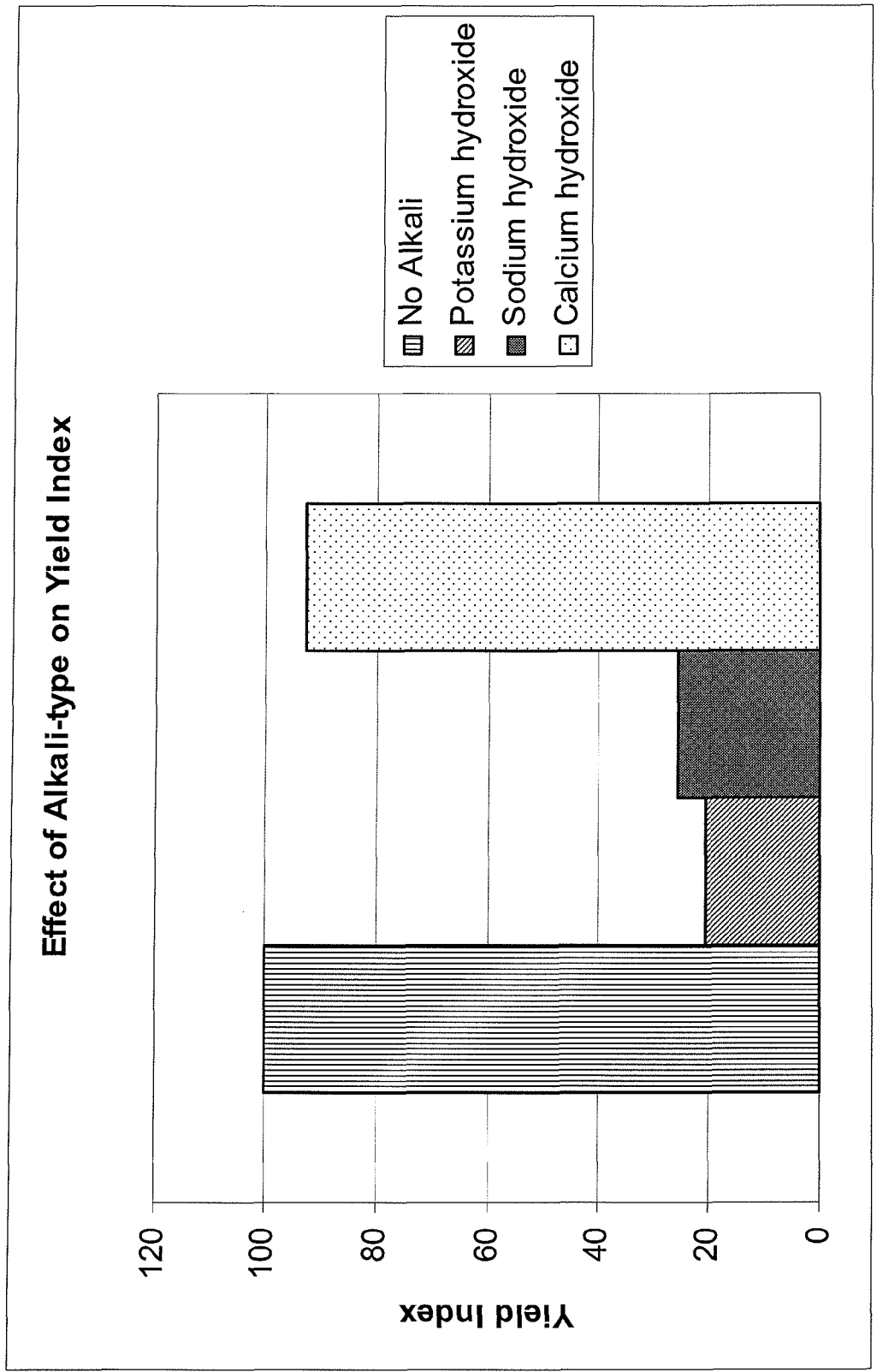
Fig. 9: Effect of alkali type on yield index.

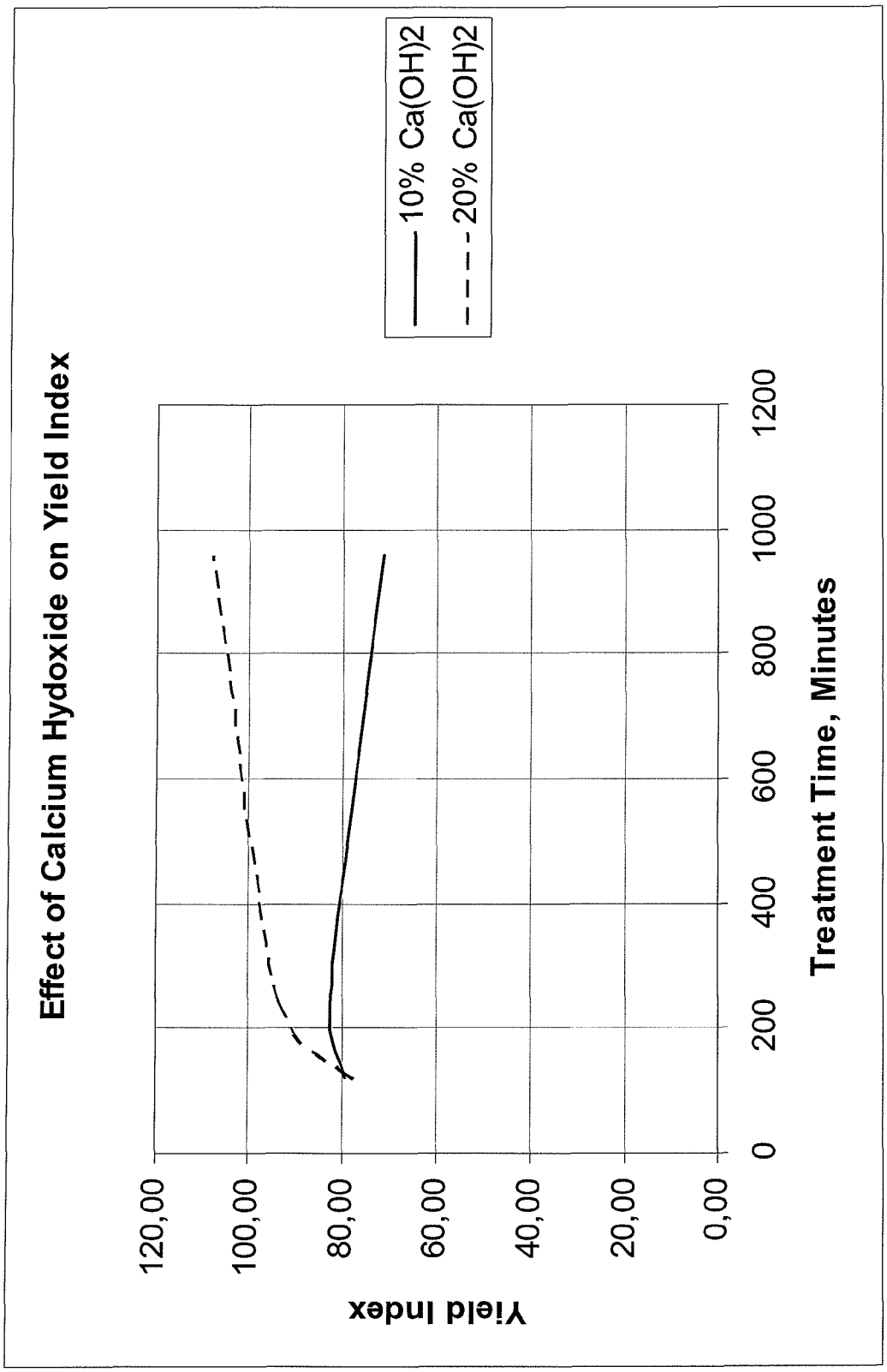
Fig. 10: Effect of treatment with calcium hydroxide on yield index.

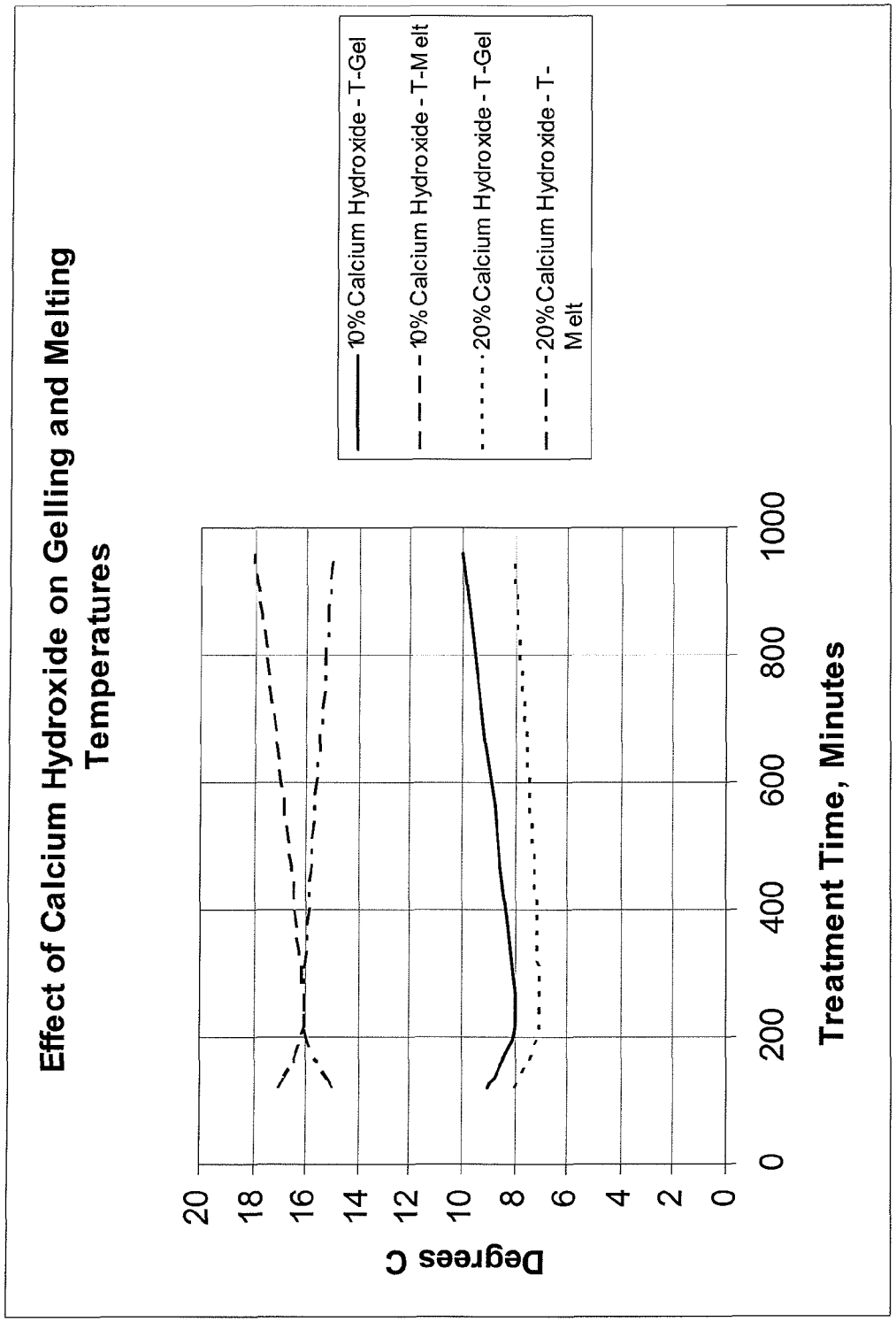
Fig.11: Effect of calcium hydroxide treatment time on gelling and melting temperatures.

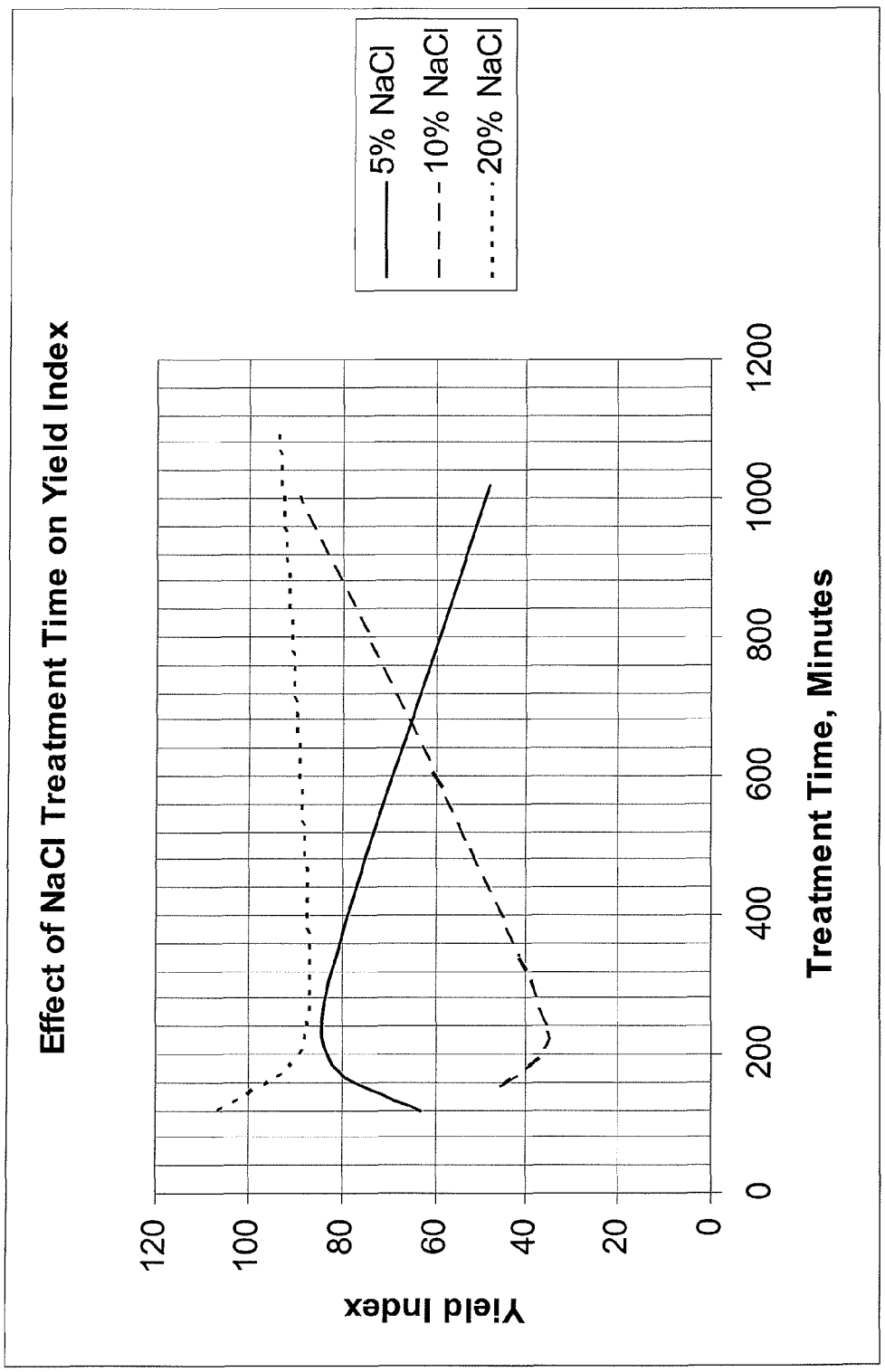
Fig. 12: Effect of sodium chloride treatment time on yield index.

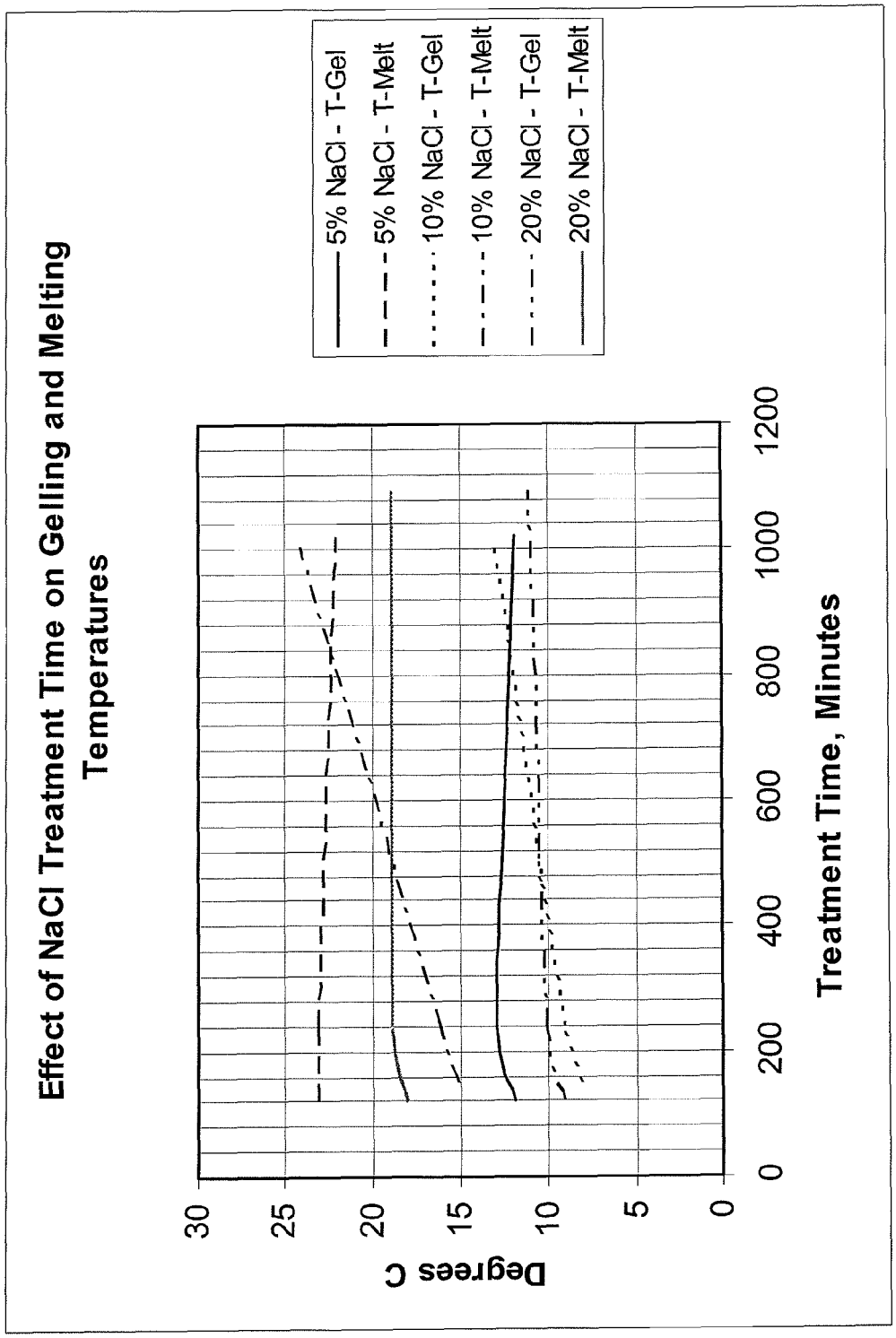
Fig. 13: Effect of sodium chloride treatment time on gelling and melting temperatures.

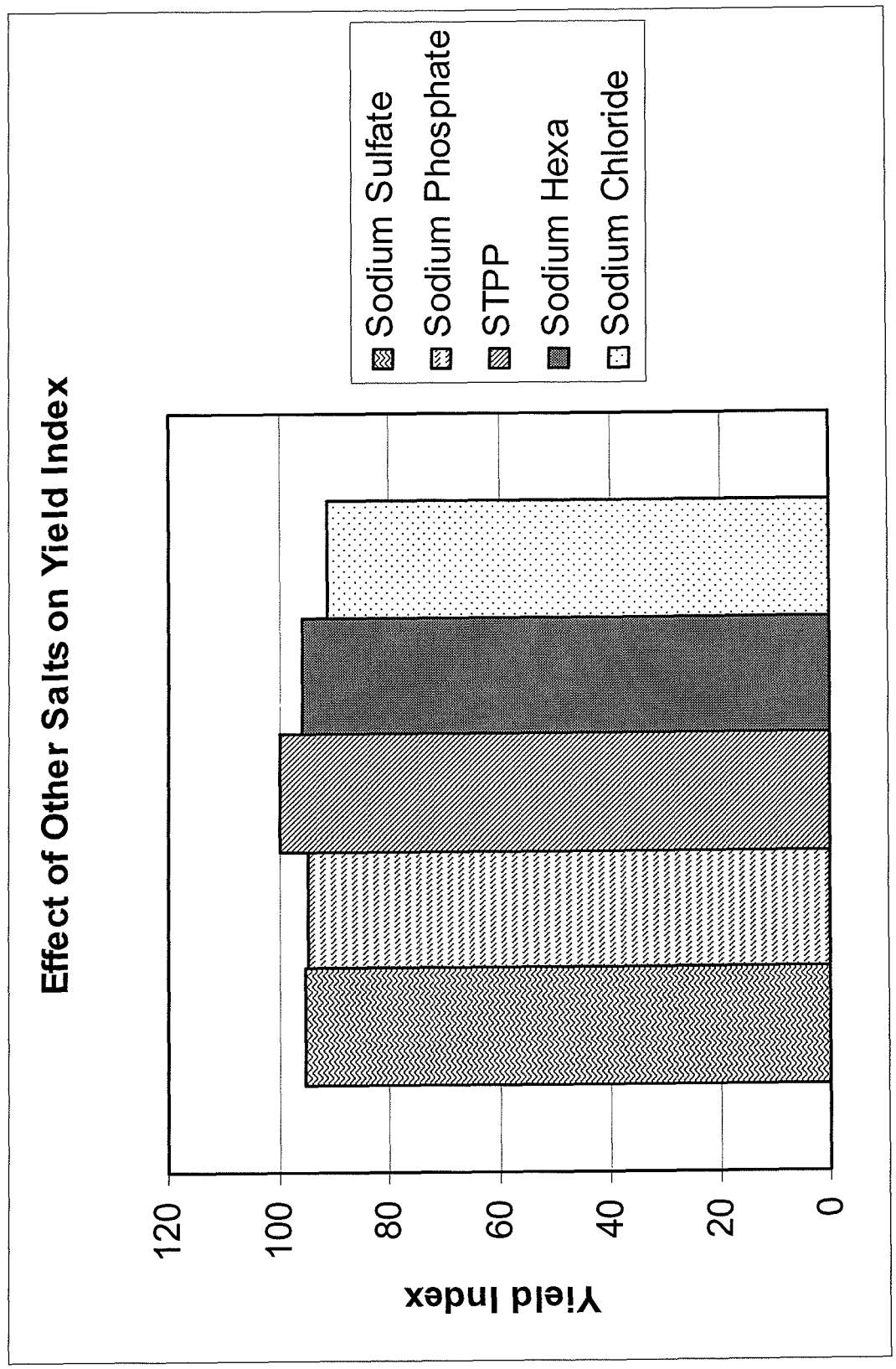
Fig. 14: Effect of various salts on the yield index.

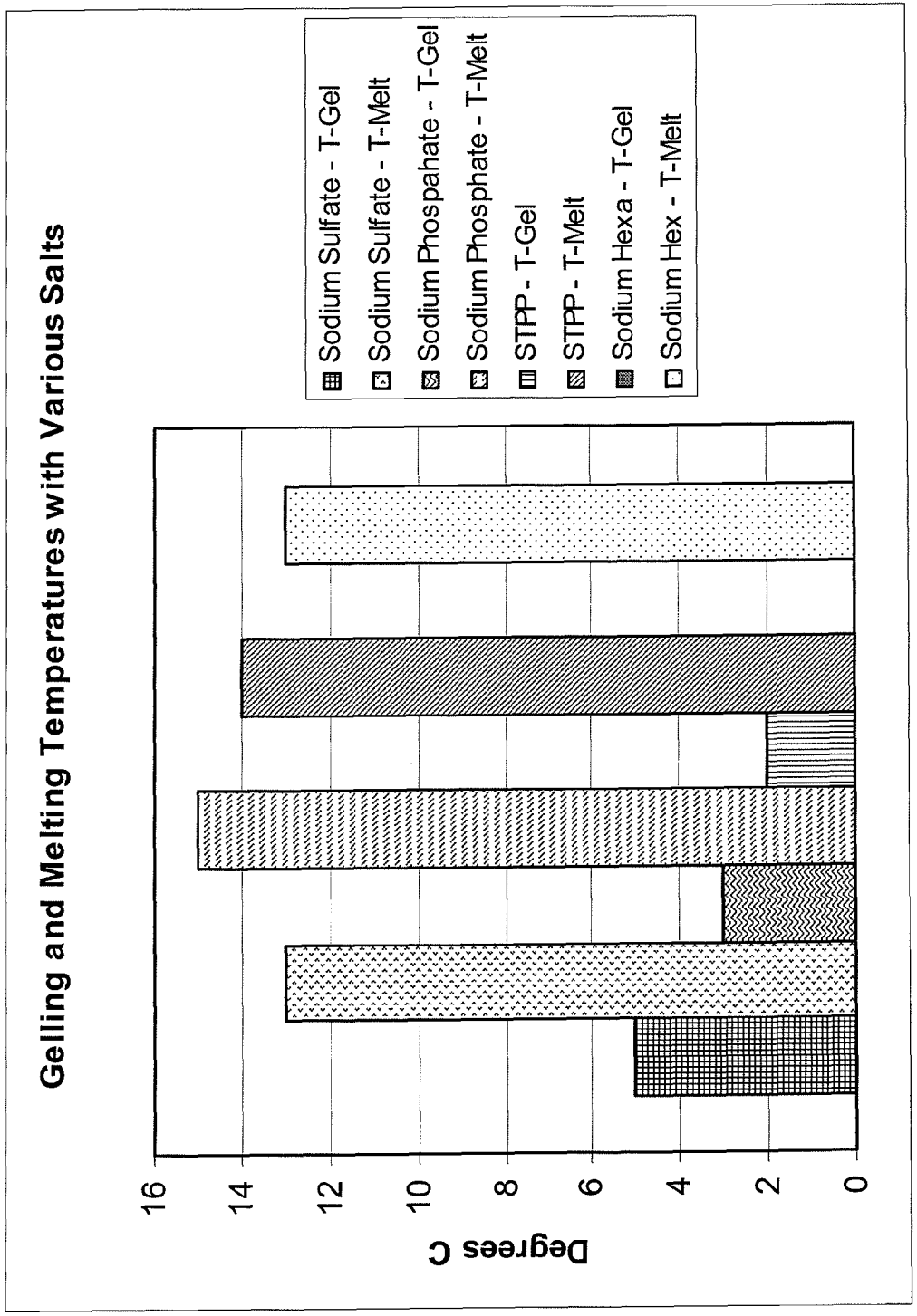
Fig. 15: Effect of various salts on gelling and melting temperatures.

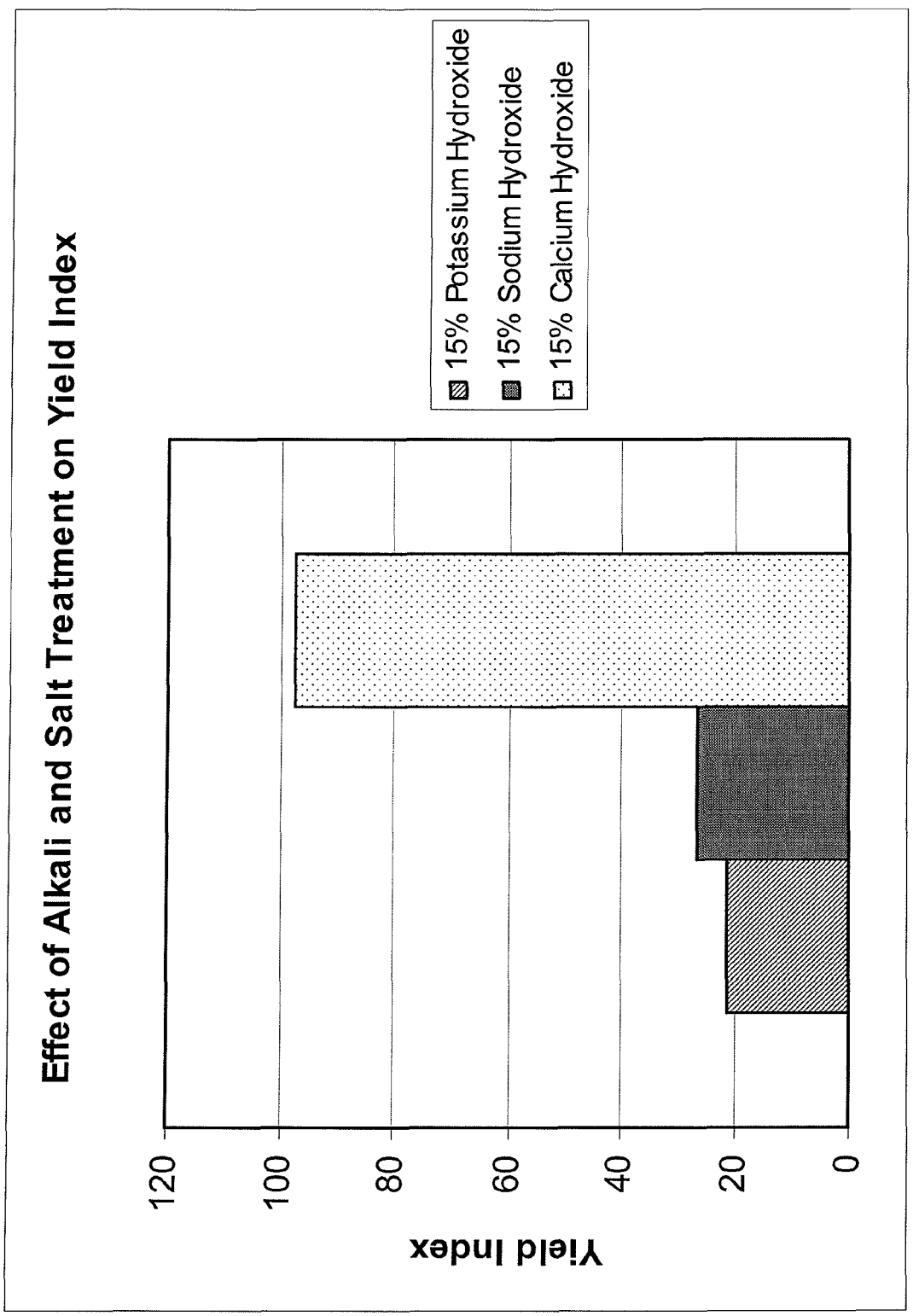
Fig. 16: Effect of treatment with alkali and salt on yield index.

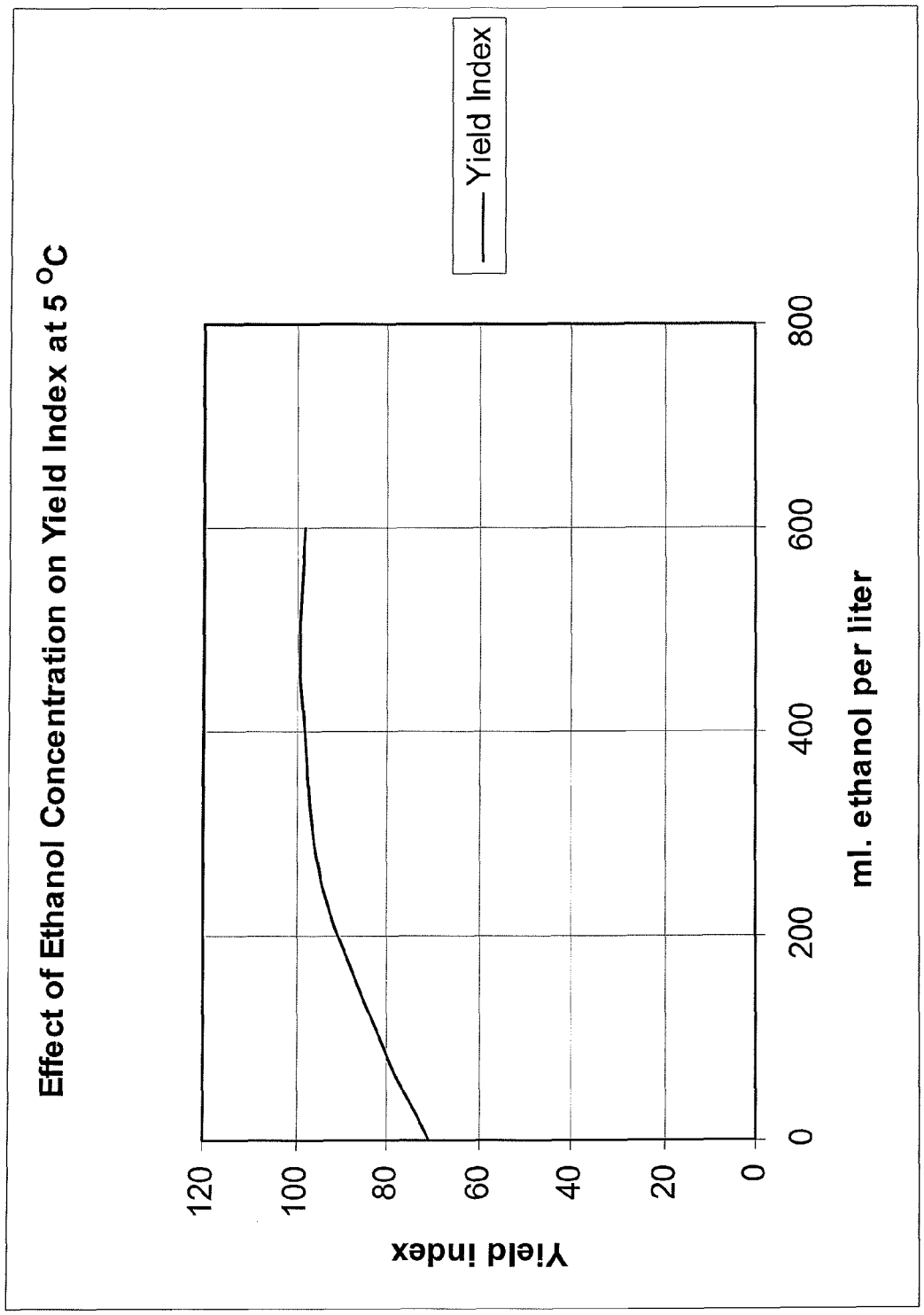
Fig. 17: Effect of alcohol concentration during alkali treatment on yield index.

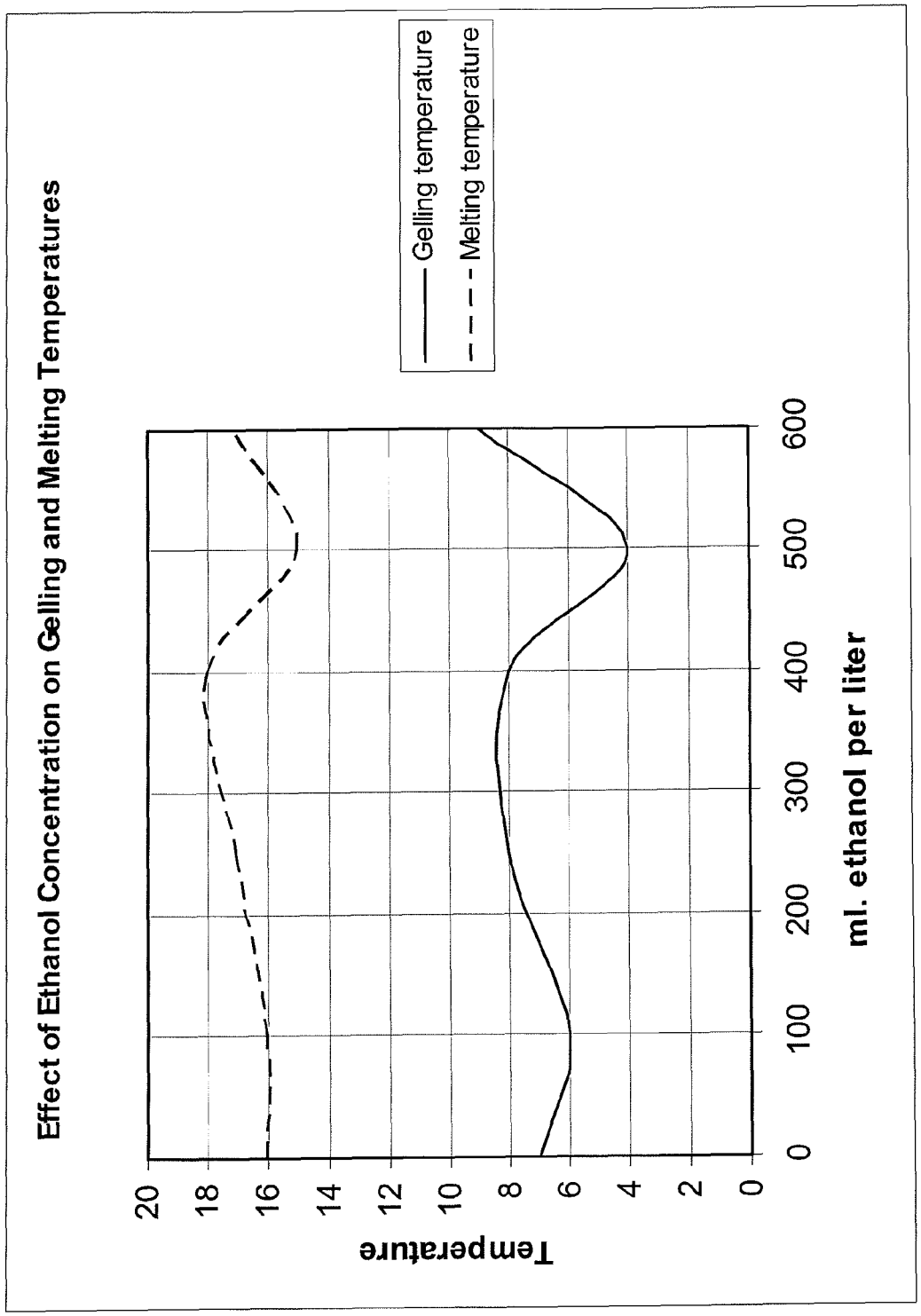
Fig. 18: Effect of alcohol concentration during alkali treatment on gelling and melting temperatures.

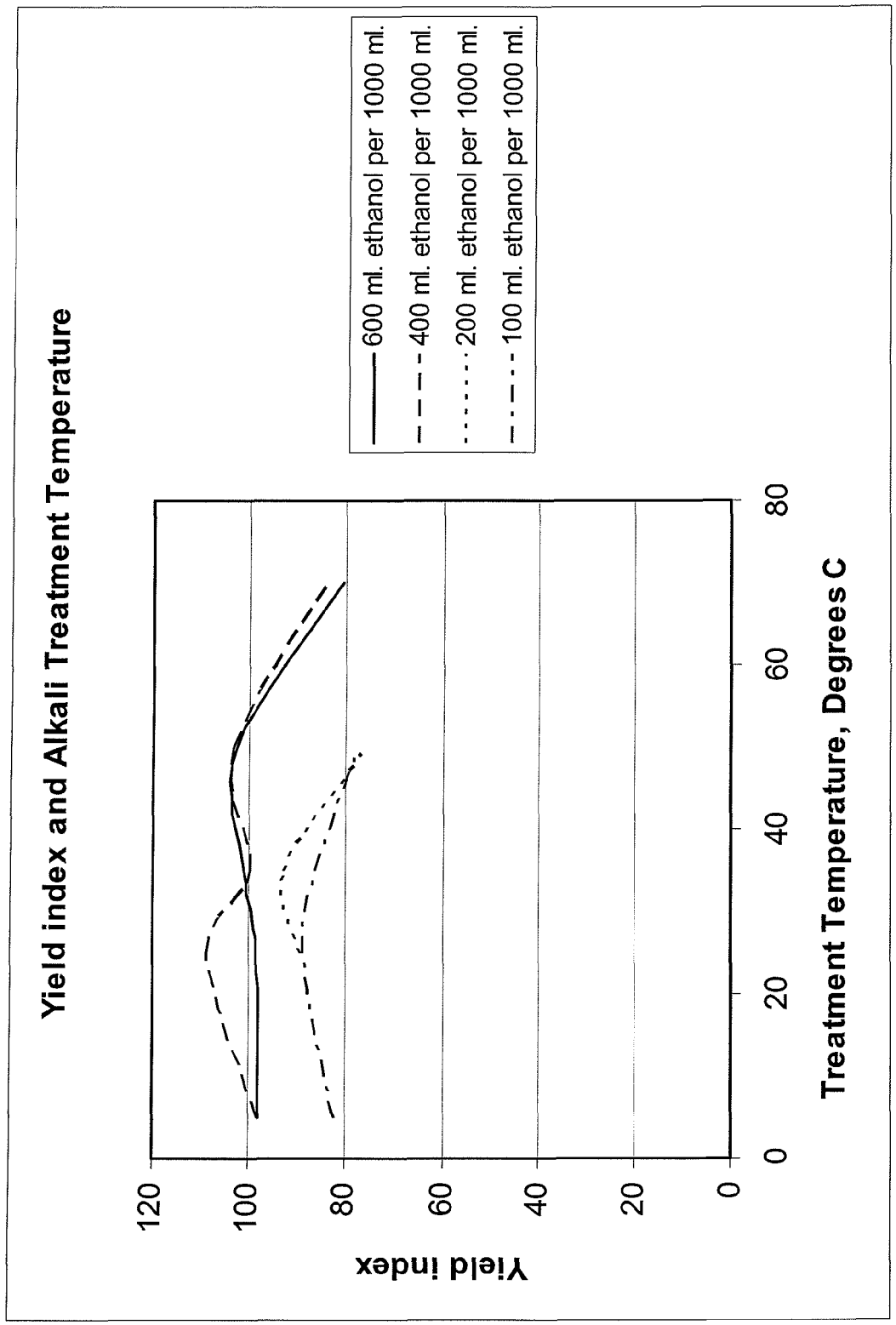
Fig. 19: Effect of alkali treatment temperature and alcohol concentration on yield index.

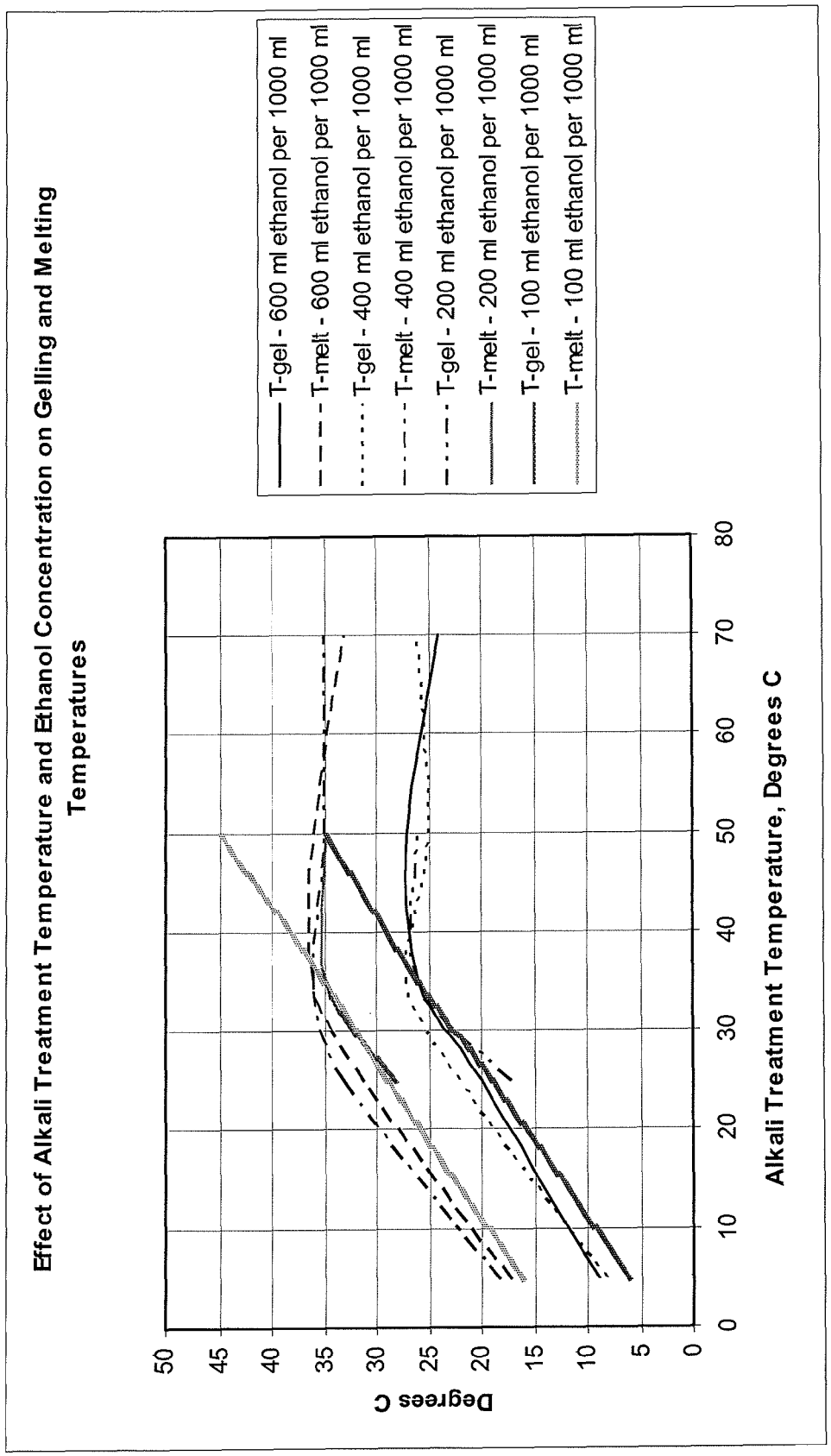
Fig. 20: Effect of alkali treatment temperature and alcohol concentration during alkali treatment on gelling and melting temperatures.

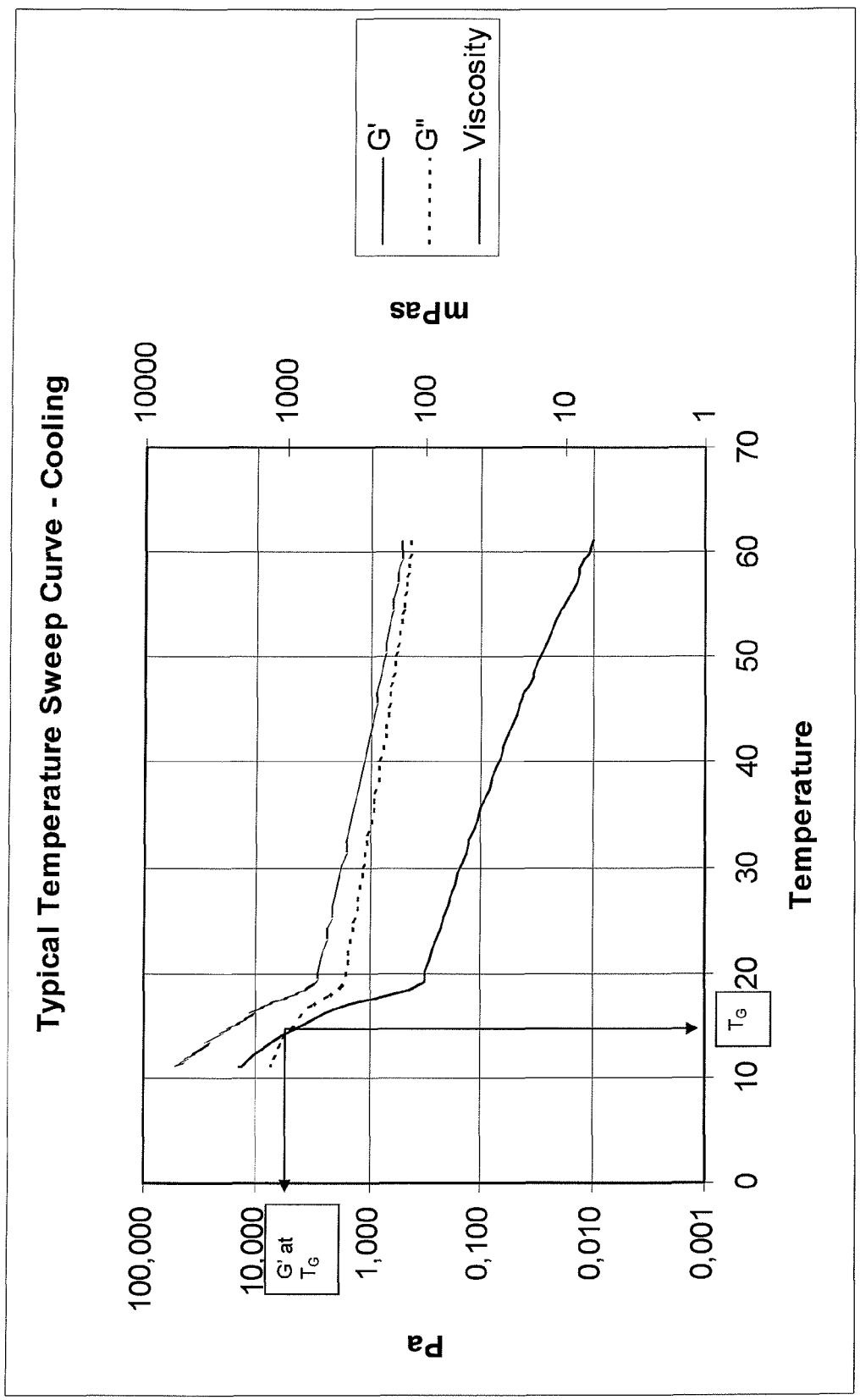
Fig. 21: Typical temperature sweep curve to determine gelling temperature and elastic modules at that gelling temperature.

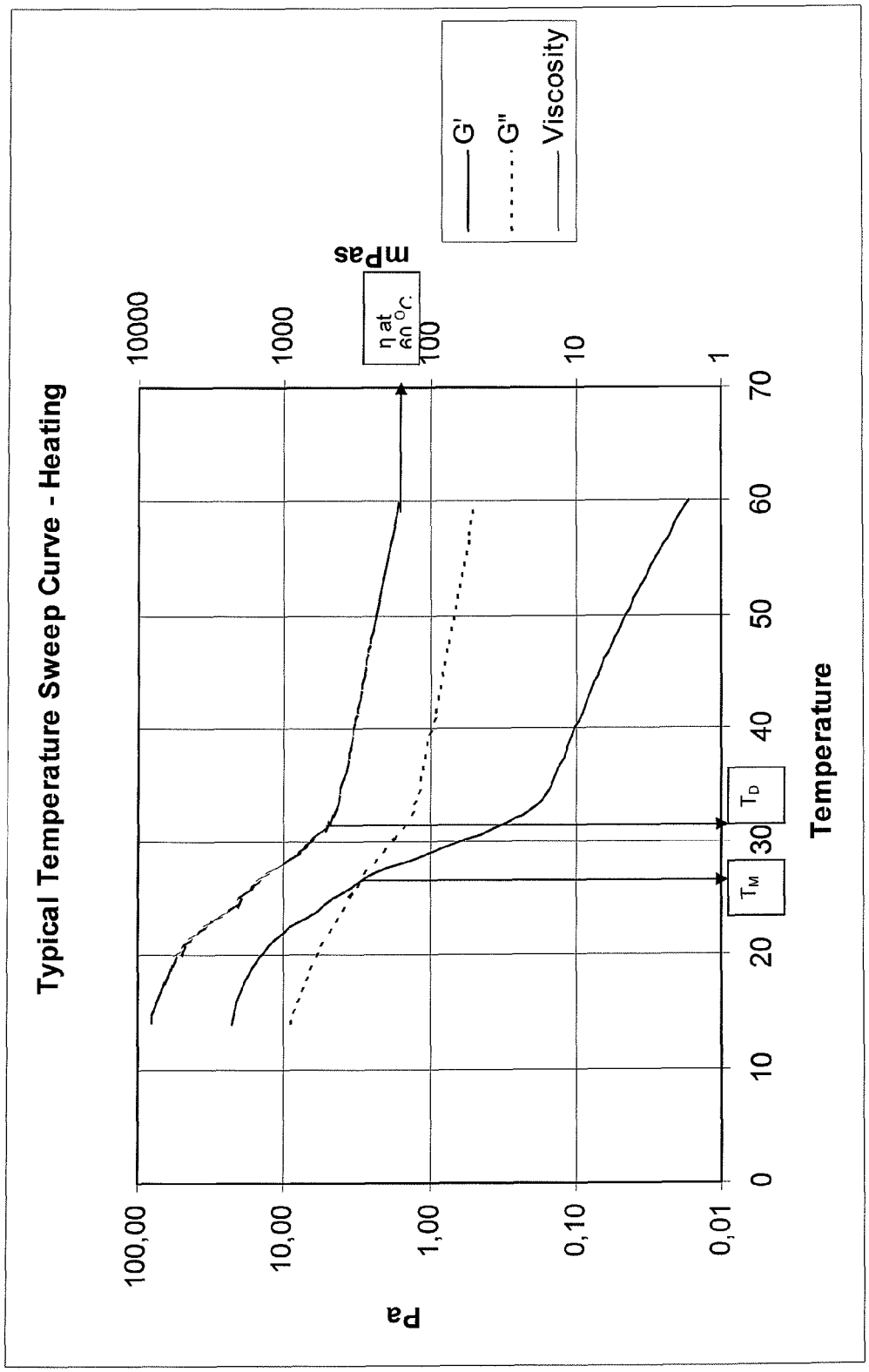
Fig. 22: Typical temperature sweep curve to determine melting temperature, dissolution temperature and viscosity at 60 °C.

CARRAGEENAN AND CARRAGEENAN-CONTAINING PRODUCTS

BACKGROUND OF THE INVENTION

Production of carrageenan can be traced back to Ireland where plants of the red seaweed algae species *chondrus crispus* were first harvested with rakes during low tide or by gathering seaweed that had washed ashore. After harvesting, the weeds were typically washed, sun-bleached, dried and boiled with milk to form a pudding. The weeds themselves were dubbed "Irish Moss" and after making it familiar to most of Europe, Nineteenth Century Irish immigrants carried it to the U.S. and Canada as well.

Today, this seaweed pudding is mostly confined to Ireland's cultural history, but carrageenan has become much more important because of its effectiveness as a functional food additive in forming gels in an aqueous system, which make it useful in a wide variety of applications, including beer (in which it has been used for over 150 years as a fining) to processed meat and food products like milk drinks and deserts; pharmaceutical preparations such as orally-administered gelcaps; personal care products such as toothpaste and skin care preparations; and household products such air-freshener gel and cleaning gels. The temperature at which carrageenan gels and melts is dependent on a number of factors that include especially the concentration of gelling cations such as potassium and calcium ions. Generally speaking, the higher the concentration of gelling cations the higher the gelling and melting temperature of the carrageenan. Such cations may come not only from the composition to which the carrageenan is added as a gelling agent, but also from the carrageenan itself.

Thus, carrageenans with relatively high gelling cation concentrations also require relatively high-temperature processing. Generally, lower temperature processes are preferred since these save processing time, are less expensive and don't negatively affect the preparation of the composition in which the carrageenan is being included—this is especially important for food compositions, where higher temperatures may impair the base foodstuffs that are included in the food product. Thus, in order to produce carrageenan materials that promote gelling at even lower temperatures there is a continuing need for carrageenan extraction methods that reduce the concentration of gelling cations in the carrageenan.

Contemporary methods of carrageenan extraction and production have advanced considerably in the last fifty years. Perhaps most significantly is that today, rather than being gathered from wild-grown seaweed, carrageenan-containing plants such as *Kappaphycus cottonii* (*Kappaphycus alvarezii*), *Euchema spinosum* (*Euchema denticulatum*), and the above mentioned *Chondrus crispus* are more commonly seeded along nylon ropes and harvested in massive aquaculture farming operations particularly in parts of the Mediterranean and throughout much of the Indian Ocean and along the Asian Pacific Ocean Coastline. Just as in the Nineteenth-century process, in contemporary processes before further processing the seaweed raw materials are first thoroughly cleaned in water to remove impurities and then dried. Then, as described in U.S. Pat. No. 3,094,517 to Stanley et al. the carrageenan is extracted from the cleaned seaweed while also at the same time being subjected to alkali modification by placing the seaweed in solution made slightly alkaline by the addition of a low concentration of alkali salt (i.e., a pH of the solution is raised to a range of, e.g., 9-10) and then heating this solution to a temperature of around 80° C. for a period of time of about 20 minutes to as long as two hours.

Subjecting the carrageenan-containing seaweed to alkali modification has the desired result of reducing the gelling cation concentration in the resulting carrageenan product; however, the extent to which the gelling cation levels can be reduced is limited because only relatively low concentrations of alkali may be used so as to not depolymerise (and thus damage) the carrageenan in the seaweed. So even though the gelling cation concentrations are reduced, they still remain high.

For example, when an alkali modification process is NOT used, typical cation concentration levels are:
Potassium: About 4%
Calcium: About 0.6%
Magnesium: About 0.7%
Sodium: About 3%

When an alkali modification step is used to reduce these gelling cation
concentrations, such as in U.S. Pat. No. 3,094,517 (Stanley et al.), which makes use of calcium hydroxide as alkali modification agent, the resulting cation concentration levels are:
Potassium: About 5%
Calcium: About 3%
Magnesium: About 0.1%
Sodium: About 2%

As can be seen, the alkali modification step taught in U.S. Pat. No. 3,094,517 significantly reduced the levels of magnesium and sodium ions, but not other gelling cations such as potassium and calcium. Accordingly, other alkalis have been proposed. For example in U.S. Pat. No. 6,063,915 to Hansen et al., sodium hydroxide and sodium bicarbonate were used as alkalis, producing carrageenans with the following cation concentrations:
Potassium: About 5%
Calcium: About 0.05%
Magnesium: About 0.01%
Sodium: About 5%

While the process taught in U.S. Pat. No. 6,063,915 produces the carrageenan
having the best cation gelling concentration profile currently available, the levels of other gelling cations are still somewhat high, making it impossible to further reduce the gelling and melting temperature of compositions containing the carrageenans.

Given the foregoing there is a need in the art for carrageenans having reduced gelling cations, and thereby lower gelling and melting temperatures, but without having been depolymerised or damaged so as to be non-functional.

BRIEF SUMMARY OF THE INVENTION

The present invention relates to a carrageenan composition comprising: sodium in the range of about 5.410 to about 8.230%, preferably about 6.300 to about 8.230%, and more preferably about 7.380 to about 8.230%; potassium in the range of about 0.023% to about 0.248%, preferably about 0.023 to about 0.238%, and more preferably about 0.023 to about 0.078%; calcium in the range of 0.046-0.553%, preferably 0.046-0.446%, and more preferably 0.046-0.325%; and magnesium in the range of about 0.051 to about 0.338%, preferably about 0.051 to about 0.244% and more preferably about 0.051 to about 0.127%; wherein the carrageenan product has a gelling temperature of 7-30° C., preferably 7-18° C., more preferably 7-12° C.; and a melting temperature in the range 16-38° C., preferably 16-28° C., more preferably 16-24° C.

Also disclosed is a carrageenan composition comprising sodium in the range of about 7.200 to about 10.120%, preferably about 7.360 to about 10.120%, more preferably 7.860-10.120%; potassium in the range of about 0.030 to about 0.330%, preferably about 0.030 to about 0.140% and most preferably about 0.030 to about 0.057%; calcium in the range of about 0.055 to about 0.574%, preferably about 0.055 to about 0.450% and more preferably about 0.055 to about 0.330%; and magnesium in the range of about 0.019 to about 0.110%, preferably about 0.019 to about 0.090%, and more preferably about 0.019 to about 0.073%; wherein the carrageenan product has a gelling temperature in the range 0-13° C., preferably 0-8° C., more preferably 0-5° C.; and a melting temperature in the range 13-24° C., preferably 13-15° C.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 shows the effect of the cleaning temperature on the product yield.

FIG. 2 shows the effect of the cleaning temperature on gelling and melting temperatures.

FIG. 3 shows the effect of the number of cleaning steps on yield index.

FIG. 4 shows the effect of the number of cleaning steps on gelling and melting temperatures.

FIG. 5 shows the effect of ethanol concentration during washing on the yield.

FIG. 6 shows the effect of ethanol concentration during washing on gelling and melting temperatures.

FIG. 7 shows the effect of the alkali treatment time on the yield.

FIG. 8 shows the effect of the alkali treatment time on gelling and melting temperatures.

FIG. 9 shows the effect of the alkali type on yield.

FIG. 10 shows the effect of treatment with calcium hydroxide on yield.

FIG. 11 shows the effect of calcium hydroxide treatment time on gelling and melting temperatures.

FIG. 12 shows the effect of sodium chloride treatment time on yield.

FIG. 13 shows the effect of sodium chloride treatment time on gelling and melting temperatures.

FIG. 14 shows the effect of various salts on the yield index.

FIG. 15 shows the effect of various salts on gelling and melting temperatures.

FIG. 16 shows the effect of treatment with alkali and salt on the yield,

FIG. 17 shows the effect of the alcohol concentration during alkali treatment on the yield.

FIG. 18 shows the effect of the alcohol concentration during alkali treatment on gelling and melting temperatures.

FIG. 19 shows the effect of the temperature during alkali treatment at various concentration of alcohol on yield index.

FIG. 20 shows the effect of the temperature during alkali treatment at various concentrations of alcohol on gelling and melting temperatures.

FIG. 21 shows a temperature sweep graph.

FIG. 22 shows a temperature sweep graph.

DETAILED DESCRIPTION OF THE INVENTION

All parts, percentages and ratios used herein are expressed by weight unless otherwise specified. All documents cited herein are incorporated by reference.

By "alkali" it is meant a base according to the Brønsted-Lowry definition, i.e., an alkali is a molecule or ion that accepts a proton in a proton-transfer reaction.

The present invention is directed to iota carrageenans, which may be more specifically described as generic repeating galactose and 3,6-anhydrogalactose residues linked b-(1-4) and a-(1-3), respectively and with characteristic 4-linked 3,6-anhydro-a-D-galactose-2-sulphate and 3-linked-b-D-galactose-4-sulphate groups. The molecules arrange themselves in a right-handed double helix with the strands parallel and threefold. The helix is stabilized by interchain hydrogen bonds through the only unsubstituted positions at O-2 and O-6 with the sulphate groups projecting outward from the helix. As mentioned above, there is a strong correlation between the presence of gelling cations and gellation. Without being limited by theory, it is believed that gels are formed in iota carrageenan through gelling (primarily monovalent) cations such as Na, K, Rh, Cs, $NH_4$, $Ca^{2+}$ as well as some divalent cations like calcium atoms that facilitate side-by-side interaction of the strands to form a three dimensional gel network. The exact transformation mechanism from the carrageenan as randomly-oriented coils at higher temperatures to a gelled network is the subject of some dispute. As the temperature is lowered the random coils of carrageenan molecules reaggregate to form gels. In one model of gellation, a gel is created by the formation of the carrageenan molecules into double helices; in certain forms of carrageenan (such as kappa carrageenan) these double helices may themselves aggregate side-by-side due to the influence of the aforementioned gelling cations forming aggregates of double helices and eventually even forming domains of a three-dimensional ordered gel network. Alternatively it has been suggested that upon cooling the random coils of the carrageenan molecules do not form double helices but only single helix structures, and that these single helix structures form single helices in which the gelling cations nested in the bends of the helix promote intermolecular aggregation.

Accordingly, the present invention is directed towards iota carrageenans produced by a process for treating fresh or dried iota carrageenan-containing seaweed so as to substantially reduce to amount of gelling cations from the iota carrageenan in the seaweed. Of equal importance is that this treatment process reduces the gelling cation concentration without extracting the carrageenan; in other words, depleting the gelling cations of the carrageenan by performing the alkali modification process essentially in situ. By modifying the polymer in si hi in the seaweed, depolymerisation of the carrageenan polymer is avoided and a iota carrageenan preparation is produced that forms gels having lower gelling and melting temperatures than were hitherto known.

The process for producing iota carrageenans according to the present invention will now be described in greater detail.

The present process utilizes a first step which is a conventional cleaning step
in which the carrageenan-containing seaweed, particularly seaweed of the species *Euchema spinosum*, is washed to remove impurities and unwanted particulates. The water may be sea water, tap water, rain water, deionised water, sodium chloride softened water or preferably demineralised water. Washing may be conducted at temperatures in the range 5-25° C. The washing may be conducted as a counter current wash or a batch wash, with a counter current process preferred because of its better utilisation of the treatment liquid. (In all subsequent steps of the process of the present invention, the water may be rain water, deionised water, sodium chloride softened water, but preferably demineralised water).

The second step in the process may be practiced in accordance with three different embodiments.

(a) Second Step, First Embodiment

In the first embodiment, the second step is a treatment of the cleaned seaweed with an aqueous treatment solution containing alkali in water. The alkali provides cations, which exclude potassium, calcium and/or magnesium in the carrageenan, while the concentration of the alkali in the treatment solution is held sufficiently high to reduce the aqueous solubility of the carrageenan thus preventing it from leaching out of the seaweed and dissolving into the water during this and subsequent steps.

Accordingly, by treating the carrageenan-containing seaweed in this way, the carrageenan is depleted from its gelling cat ions in situ.

Preferred alkalis are sodium hydroxide and its corresponding carbonates and bicarbonates, with sodium hydroxide being the most preferred. Sodium hydroxide is particularly notable for reducing the gelling and melting temperatures of carrageenan. Also suitable is calcium hydroxide. As discussed above, the concentration of the alkali must he such to provide sufficient cations while preventing solubilization of the carrageen in the water phase; an appropriate range to accomplish this dual purpose is a concentration of alkali in range of 3-30 wt %, preferably 10-25 wt % and most preferably 15-20 wt %.

In some cases alcohol may be added to the treatment solution to further reduce the leaching out of the carrageenan from the seaweed and its dissolving into water. It is particularly important to add alcohol when relatively small quantities of the aqueous treatment liquid are used. This is because excess water initially present in the wet seaweed and also remaining from the washing step could dilute the concentration of the cations in the aqueous treatment solution to the point that the carrageenan begins to leach out. The presence of alcohol in the treatment solution helps maintain high yields, especially as the treatment temperature is increased. Preferred alcohols are methanol, ethanol and isopropyl alcohol with ethanol being most preferred. The amount of alcohol ranges from 200-800 ml alcohol per 1000 ml treatment solution, preferably 200-600 ml alcohol per 1000 ml treatment solution and most preferably 500-600 ml alcohol per 1000 ml treatment solution.

The temperature during treatment ranges from 0-70° C., preferably 5-70° C. and most preferably 5-35° C. The treatment time is in the range 1-24 hours, preferably 2-17 hours, and most preferably 2-4 hours. Either a batch wise or counter current process may be used; although as mentioned above the counter current process is preferred because it makes better utilisation of the treatment liquid.

Carrageenan products prepared according to the first embodiment of the second step form gels having gelling temperatures of 7-30° C., preferably 7-18° C., more preferably 7-12° C.; and melting temperatures in the range 16-38° C., preferably 16-28° C., more preferably 16-24° C. In addition, carrageenan products according to the first embodiment of the second step are characterized by a sodium content in the range 5.410-8.230%, preferably 6.300-8.230% and more preferably 7.380-8.230%; a potassium content of 0.023%-0.248%, preferably 0.023-0.238% and more preferably 0.023-0.078%; a calcium content of 0.046-0.553%, preferably 0.046-0.446% and more preferably 0.046-0.325%; and a magnesium content of 0.051-0.338%, preferably 0.051-0.244% and more preferably 0.051-0.127%.

(b) Second Step, Second Embodiment

In a second embodiment of the present invention, the second step is a treatment of the washed seaweed with an aqueous treatment solution containing a sodium salt. The effect is similar as described above with respect to the first embodiment where the sodium salt provides monovalent cations to prevent the diffusion of potassium, calcium and magnesium ions into the carrageenan while the concentration of the sodium salt in the treatment solution is held sufficiently high to reduce the aqueous solubility of the carrageenan thus reducing its leaching out from seaweed and dissolution into water. Thus similarly as above, by treating the carrageenan-containing seaweed in this way, the carrageenan is depleted from its gelling cat ions in situ.

Sodium salts include, but are not limited to sodium chloride, sodium sulphate, sodium phosphate, sodium tri polyphosphate and sodium hexametaphosphate. The concentration of sodium salt in the water phase is in the range 3-30 wt %, preferably 10-25 wt %, and more preferably 15-20 wt %.

As described above in the section entitled "Second Step, First Embodiment", alcohol may optionally be added to the treatment solution to further reduce the leaching out of the carrageenan from the seaweed and dissolving into water. Similarly, the same temperature and time parameters are used in this embodiment of the process as in the previous two mentioned above.

In this embodiment, the temperature during treatment ranges from 0-25° C., preferably 0-10° C., and more preferably 0-5° C. The treatment time is in the range 1-24 hours, preferably 2-17 hours, and most preferably 2-4 hours. Either a batch wise or counter current process may be used; the counter current process is preferred because it makes better utilisation of the treatment liquid.

Carrageenan products prepared according to the second embodiment of the second step form gels having gelling temperatures in the range 0-13° C., preferably 0-8° C., more preferably 0-5° C.; and melting temperatures in the range 13-24° C., preferably 13-15° C. In addition, carrageenan products according to the second embodiment of the second step are characterized by a sodium content in the range 7.200-10.120%, preferably 7.360-10.120%, more preferably 7.860-10.120%; a potassium content of 0.030-0.330%, preferably 0.030-0.140% and most preferably 0.030-0.057%; a calcium content of 0.055-0.574%, preferably 0.055-0.450% and more preferably 0.055-0.330%; and a magnesium content of 0.019-0.110%, preferably 0.019-0.090%, and more preferably 0.019-0.073%.

(C) Second Step, Third Embodiment

In a third embodiment of the present invention, this second step is essentially
split, into three substeps which include a first substep of treating the washed seaweed with a first aqueous treatment solution containing about 3-30 wt %, preferably 10-25 wt %, and most preferably 15-20 wt %, of a first treatment compound, a second substep of washing or rinsing the treated seaweed to remove excess of the first treatment compound, and a third substep of treating the washed seaweed with a second aqueous treatment solution containing about 3-30 wt %, preferably 10-25 wt %, and most preferably 15-20 wt %, of a second treatment compound. (For purposes of clarity, exactness and completeness to persons of ordinary skill in the art. these substeps are referred to as separate processing steps in the claims).

The third embodiment can thus be practiced in two subembodiments. In the first subembodiment, the first treatment compound is an alkali, and the second treatment compound is an salt; in the second subembodiment, the first treatment compound is an salt, and the second treatment compound is an alkali.

As described above in the section entitled "Second Step, First Embodiment", alcohol may optionally be added to the treatment solution to further reduce the leaching out of the carrageenan from the seaweed and dissolving into water. Similarly, the same temperature and time parameters are used in this embodiment of the process as in the previous two mentioned above.

Carrageenan products according to the third embodiment of the second step produce gels having gelling temperatures in the range 4-35° C., preferably 4-25° C. and most preferably 4-9° C.; and melting temperatures in the range 15-45° C., preferably 15-35° C. and most preferably 15-18° C. In addition, carrageenan products according to the third embodiment of the second step are characterized by a sodium content in the range 6.720-7.546%, preferably 6.920-7.546% and more preferably 7.200-7.546%; a potassium content of 0.017-0.078%, preferably 0.017-0.030% and more preferably 0.017-0.026%; a calcium content of 0.140-0.250%, preferably 0.140-0.220% and most preferably 0.140-0.160%; and a magnesium content of 0.083-0.210%, preferably 0.083-0.120% and more preferably 0.083-0.094%.

Carrageenan products made according to the third embodiment are further characterized by the following gelling temperatures and melting temperatures in an air gel formulation, in demineralised water and in demineralised water containing sodium chloride:

| System | Carrageenan % | NaCl % | $T_G$ ° C. | $T_M$ ° C. |
|---|---|---|---|---|
| Air gel | 0.50 | | −5-11 | 9-27 |
| | 1.00 | | 7-26 | 20-36 |
| | 1.50 | | 18-32 | 30-40 |
| Demineralised water | 0.60 | | −15--10 | −5-0 |
| | 1.00 | | −10--5 | 0-7 |
| | 1.50 | | −5-6 | 7-15 |
| Demineralised water and NaCl | 0.60 | 1.00 | 45-55 | 50-62 |
| | 0.60 | 3.00 | 63-75 | 67-85 |
| | 0.60 | 5.00 | 74-83 | 78-87 |

Further, carrageenan products according to the third embodiment are characterized by the following gelling and melting temperatures in systems composed of demineralised water and potassium chloride or calcium chloride:

| Carrageenan % | KCl % | $CaCl_2 \cdot 2H_2O$ % | $T_G$ ° C. | $T_M$ ° C. |
|---|---|---|---|---|
| 1.00 | 0.00 | | −10--5 | 0-7 |
| | 0.04 | | −5-5 | 5-15 |
| | 0.12 | | 0-13 | 10-23 |
| | 0.16 | | 7-18 | 15-28 |
| | 0.32 | | 17-30 | 28-38 |
| 1.00 | | 0.08 | 15-34 | 30-44 |
| | | 0.16 | 42-55 | 52-61 |
| | | 0.32 | 60-74 | 67-83 |

In the third step in the process (which is common to all three embodiments of the second step discussed above) the treated seaweed is subjected to washing to remove the excess of the last reagent that was used in the second or treatment step. The reagent can be of course either an salt or an alkali. Washing is done with slow agitation and the number of washings is in the range 1-4, preferably 1-2, and washing time is in the range 10-30 minutes per wash, preferably 15 minutes per wash. Controlling the number of washing steps is important because the yield decreases with time (possible reasons for this are discussed below) and because the number of washing steps affects the gelling and melting temperatures (again, this is discussed in greater detail, below). As above to limit leaching out of the carrageenan from the seaweed the temperature during washing is held in the range 0-25° C., preferably 0-5° C.

In the fourth and final step of the process the treated seaweed can be dried and ground into a powder of semi-refined carrageenan products, which in addition to carrageenan also contain the cellulosic material from the seaweed.

Alternatively, pure carrageenan can be extracted from the treated seaweed in pure water, such as one of the water types described above (again demineralised water is preferred). Of primary importance is that the extraction step does not re-introduce the gelling cations. Extraction temperatures are in the range 0-90° C., preferably 25-90° C. and most preferably 50-90° C. Typically, higher extraction temperatures result in greater yields.

Other aspects of the processes for production of carrageenan according to the present invention are not particularly limited, and where necessary conventional carrageenan technology may be used In addition to the specific steps set forth herein, processes of the present invention may further comprise additional processes typically associated with carrageenan production.

An additional important aspect of this present invention is that because the relationship between the gelling and melting temperatures and the several processing parameters has been determined with such specificity, then these temperatures can be controlled depending on the specific properties desired in the carrageenan. In other words, by specially controlling the processing parameters, a carrageenan having particular properties can be produced.

Besides air gels, carrageenan products of the present invention have utility in applications where gelling and/or melting of gels must take place at temperatures below those provided by conventional carrageenan products. In addition, carrageenan products of the present invention also find utility in products which are heat treated at temperatures below the temperatures at which conventional carrageenan products are dissolved.

In this area, where gelling and/or melting must take place at lower temperatures than what is possible with conventional carrageenan products, applications include but are not limited to:

Air freshener gels: these gels contain one or more non-ionic surfactants, and when the gels are heated above a certain point (referred to as the "cloud point", typically non-ionic surfactants have a cloud point in the range of about 0 to about 60° C.) the non-ionic surfactants become less soluble and precipitate out of the gel leading to a cloudy, non-transparent gel. Typically, conventional carrageenan products display gelling temperatures above the cloud point of the surfactants, and thus, freeze the surfactant crystals in the gel, causing the gel to become permanently unclear even when the temperature is lowered below the cloud point. The carrageenan products of the present invention can be tailored to gel at or below the cloud point of the surfactant, thus, preventing the surfactant crystals from being froze in the gel and so preventing the resulting air freshener gel from becoming cloudy, and non-transparent.

Cold setting air freshener gels: Conventional air freshener gels are made by heating the composition to about 70-90° C., after which gelation takes place during cooling. However, the heating provides for a substantial loss of the fragrance used in the air freshener formulation as some of the fragrance material evaporates during heating. Carrageenan products of the present invention can be tailored to dissolve at temperatures at or below room temperature, which eliminates the loss of fragrances. Once dissolved, the liquid air freshener formulation can be poured into its final container, which contains gelling cations (as discussed above) that in conjunction with the carrageenan form the gel network. Such cations may be added directly into the container before filling the air freshener formulation into the container, or the cations may be added as a coating, such as a film coating, with which the container is pre-coated. As the cations diffuse into the air freshener formulation under quiescent conditions, the air freshener formulation will gel into a homogeneous gel.

Water-in-oil emulsions: Water-in-oil emulsions are characterized by a continuous oil phase in which a discontinuous phase of water droplets are dispersed. In many cases it is desired that the water-in-oil emulsion inverts into an oil-in-water emulsion at a specific temperature so that the emulsion releases its water soluble constituents. An example is margarine, where the emulsion inverts in the mouth to release water soluble aromas and salts. Gelatine is the preferred stabilizer of the water phase, since gelatine ensures that the aqueous phase melts at the same temperature as the oil phase. That temperature is about the temperature in the mouth, and thus, through the saliva and the shear in the mouth, the emulsion inverts to an oil-in-water emulsion and releases aroma and salt. Conventional carrageenan products are unable to form gels, which melt at the temperature in the mouth, but carrageenan products of the present invention can be tailored to do just that.

Similarly, most skin care lotions are produced as oil-in-water emulsions. This means that the water phase is the continuous phase, which requires that preservatives are used in skin care lotion formulations. There is a desire to eliminate preservatives in skin care lotions, particularly preservatives of the parabene type, because they have some similarity with hormones. Carrageenan products of the present invention makes it possible to provide a skin care lotion in the form of an water-in-oil emulsion, which because of the oil continuous phase does not require preservatives, but which will invert to a spreadable oil-in-water emulsion at the temperature of the skin and the shear from rubbing in the lotion.

Capsules: Soft capsules are made trough sealing of two capsule halves Gelatine is preferred because gelatine forms capsules which can sealed at low temperatures through the low melting temperature of gelatine gels. There is, however, a desire for an alternative to gelatine that meets the dietary guidelines of vegetarians, Jewish kosher, and halai practitioners, and is not derived from meat products association with Bovine Spongiform Encephalopathy. Prior art carrageenan products could not be used in this application because they form gels with much higher melting temperatures. But Carrageenan products of the present invention can be tailored to form gels, which melt at the same or even lower temperatures than gelatine gels.

Encapsulation: Encapsulation is used in areas such as flavour encapsulation and encapsulation of drugs. In cases where the agent being encapsulated are heat sensitive, carrageenan products of the present invention can encapsulate the agent at low temperatures. Similarly, the encapsulated ingredient can be released at any temperature in the range from below 0° C. and up to about 75° C., preferably about 30° C. to about 40° C. depending on the composition of the encapsulating formulation.

Processed meat, poultry and fish products: Processed meat, poultry and fish products are often heat treated at pasteurization temperature, which is about 72° C. The aqueous phase of such products typically contain up to about 3% sodium chloride, which precludes the dissolution of conventional carrageenan products. Carrageenan products of the present invention can be tailored to dissolve at a temperature at or below the pasteurization temperature, which leads to dissolution of the carrageenan product and thus, a more homogeneous gel in the final processed meat, poultry or fish product.

Dentifrice and Toothpaste Products: As a result of the increased solubility of the carrageenan, the result is a of the present invention provide for higher viscosity due to an increased solubility because When more carrageenan goes into solution, there is more reactive carrageenan to form a viscous paste together with the other ingredients in the toothpaste formulation. These ingredients are primarily the humectant and the salts.

The present invention will now be explained in greater details with respect to the following several experiments. These experiments and their accompanying textual descriptions, will present detailed descriptions of the process of the present invention as well as results obtained from the experimental process. Additionally analysis of the results will be presented and supplemented by possible theoretical explanations. The following experimental equipment, materials and methods were used in carrying out the present experiments. Application of these experimental methods are introduced in the specific examples section below that illustrate the present invention and place it within the context of the prior art.

Equipment

Hobart mixer equipped with heating and cooling jacket and stirrer—Hobart N-50G produced by Hobart Corporation, USA.

Cooling unit capable of cooling to about 5° C. , e.g., the Haake K10/Haake DC10 produced by Thermo Electron GmbH, Germany.

Magnetic stirrer and heater equipped with temperature control, e.g., Ikamag Ret produced by Janke & Kunkel GmbH, Germany.

Beakers, 1 liter and 2 liters.

2 liters conical flask, Buchner funnel and vacuum pump.

Filter cloth.

Rheometer—Haake RheoStress RS100 equipped with cup Z20/48 mm and rotor Z20 DIN produced by Thermo Electron GmbH, Germany.

pH-meter—PHM220 produced by Radiometer, Denmark

Analytical balance, weighing with two decimals—Sartorius Basic B3100P produced by Sartorius GmbH, Germany.

Chemicals:

Sodium chloride, analytical, Merck KGaA, Darmstadt, Germany

Calcium chloride dehydrate, analytical, Merck, Germany

Sodium hydroxide, analytical, Merck, Germany

Potassium hydroxide, analytical, Merck

Calcium hydroxide, analytical, Merck

Sodium sulphate, analytical, Merck

Sodium methyl-4-hydroxybenzoate, analytical, Merck

Potassium chloride, analytical, Merck
Tri sodium phosphate dodecahydrat, analytical, Merck
Ethanol, 96%
Methanol, 100%
Isopropyl alcohol, 100%
Potassium chloride, analytical, Merck
Glycerine, analytical, Scharlau Chemie, Barcelona, Spain
Lemon oil, H.N. Fusgaard, Roedovre, Denmark
Cremophor RH 40, BASF, Ludwigshafen, Germany Treatment of Seaweed:
1. Seaweed was washed three times in 1 liter demineralized water and refrigerated.
2. This washed seaweed was then placed in a 2-liter beaker.
3. A treatment solution was formed by the salt or alkali was dissolved at room temperature in 1000 ml of demineralized water, and subsequently cooled to the treatment temperature.
4. Seaweed was added to the treatment solution.
5. Seaweed was treated at specific temperatures and times (see below) while being stirred.
6. Treated seaweed was washed in demineralized water at specific temperatures and times (see below).
7. The washed seaweed was extracted in 1500 ml. demineralized water at 90° C. for 1 hour.
8. The extract was filtered on diatomaceous earth.
9. The filtered extract was precipitated in three volumes 100% IPA and the precipitate was washed in 1 liter 100% IPA.
10. The washed precipitate was dried at 70° C. overnight.
11. The dry precipitate was milled on 0.25 mm screen.

The Determination of gelling and melting temperatures of carrageenan-compositions was made using a composition with the following carrageen-incorporating composition:

| Ingredients | Grams | % |
| --- | --- | --- |
| Seaweed extract | 0.48 | 0.96 |
| Glycerine | 3.00 | 6.00 |
| Parabene | 0.05 | 0.10 |
| Demineralized Water | 33.75 | 67.50 |
| Lemon oil | 1.25 | 2.50 |
| Isopropyl alcohol | 1.50 | 3.00 |
| Cremophor RH 40 | 10.00 | 20.00 |
| Net weight | 50.00 | 100.00 |

This composition was prepared as follows:
1. The water, glycerine and parabene were mixed.
2. The seaweed extract was dispersed in this mixture and stirred for about 60 minutes.
3. The dispersion was heated while stirring to 70° C.
4. The dispersion was then cooled to 55-60° C.
5. A hot (about 50° C.) preparation of oil, isopropyl alcohol and Cremophor RH 40 was mixed into the cooled dispersion.
6. The net weight was adjusted with hot (about 60° C.) water and cooled over night at room temperature.

The gelling and melting temperatures were measured by temperature sweeps on Haake RheoStress RS100, using cooling and heating rates of 1° C./min. The following program was generally used, however, in some instances where gelling and melting temperatures were higher; the program was run at higher starting temperatures and lower end-temperatures:
1. 65-5° C., 0.50 Pa, f=0.4640 Hz
2. 5-65° C., 0.50 Pa, f=0.4640 Hz
3. Gelling temperature is defined as the temperature during the cooling sweep, where the elastic modulus, G' intersects with the viscous modulus, G".
4. Melting temperature is defined as the temperature during the heating sweep, where the elastic modulus, G' intersects with the viscous modulus, G".

FIG. A and FIG. B show typical temperature sweep graphs.

The following procedure was used for gelling and melting temperatures in demineralized water:
1. The carrageenan product was added slowly at room temperature to demineralized water while stirring on magnetic stirrer. Stirring was continued until the preparation was completely lump-free.
2. The preparation was then heated while stirring on magnetic stirrer to 70° C., and left to cool at room temperature.

The following procedure for gelling and melting temperatures in demineralized water with salts;
1. The salt was dissolved in demineralized water at room temperature.
2. The carrageenan product was added slowly to the salt solution at room temperature while stirring on magnetic stirrer.
3. The preparation was then heated while stirring on magnetic stirrer to up to 90° C., and left to cool at room temperature.

The Viscosity in Toothpaste was measured using the following equipment, chemicals, formula, and procedure:

Equipment
1. Beaker, 100, l
2. Beaker, 150 ml, height 95 mm, diameter 50 mm
3. Analytical balance
4. Laboratory scale, max load: 7000 g, precision: 0.1 g
5. Electric stirrer, Janke and Kunkel GmbH type RW20
6. Household mixer, Hobart type N-50
7. Brookfield viscosimeter RVT
8. Brookfield Helipath Stand D
9. Low temperature incubator, 25° C.
10. High temperature incubator, 50° C.
11. Thermostatically controlled water bath at 25° C., Haake F3-K
12. Nesco film
13. Stop watch
14. Plastic lids Chemicals
Glycerol, 100%
Dicalcium phosphate dehydrate, $CaHPO_4$, $2H_2O$
Tetra sodium pyrophosphate decahydrate, $Na_4O_7P_2$, $10H_2O$, Sieved through a 40 mesh
Sodium chloride, NaCl Formula

| | |
| --- | --- |
| Carrageenan product | 6.60 g |
| Glycerol | 220.00 g |
| Dicalcium phosphate dehydrate | 480.00 g |
| Tetra sodium pyrophosphate decahydrate | 4.20 g |
| Sodium chloride | 6.70 g |
| Deionized water | 282.50 g |
| Total | 1000.00 g |

Process
1. Carrageenan product was dispersed in glycerol in exactly 3 minutes while stirring with a propeller stirrer (200-400 rpm), which was stirred for another 10 minutes (400 rpm).
2. Additional water was added while stirring (800 rpm). And the speed increased to 1200 rpm after 5 minutes and then mixed for another 10 minutes.
3. The solution was transferred to the household mixer quantitatively.
4. The tetra sodium pyrophosphate was added during mixing (speed 1) and stirred for 5 minutes (speed 2).

5. The di calcium phosphate dehydrate was added at speed 1 and mixed for 15 minutes (speed 2). The bowl and blade was scraped after 1, 5 and 10 minutes respectively.
6. The sodium chloride was added and mixed for 25 minutes (speed 2). The bowl and blade was scraped after 5, 10 and 15 minutes respectively while maintaining a smooth texture to the paste.
7. The paste was placed into four 150 ml beakers and covered with plastic lids making sure that as little air as possible is introduced in the paste during filling.
8. The 4 beakers were placed in a water bath which was pre-adjusted to 25° C.—for 1 hour—while making sure that all of the paste in the beakers was below the water level.
9. The toothpastes were covered tightly with Nesco-film.
10. Two beakers were then placed in the low-temperature incubator (adjusted to 25° C.) and two beakers were placed in a high-temperature incubator (adjusted to 50° C.),
11. After 3 days' storage, one beaker was transferred from the high-temperature incubator to a 25° C. water bath and kept there for 1 hour. Viscosity was measured 72 hours after the start of the incubation.
12. There was then a measurement of the two 3-days viscosities at 25° C. (after storage at 25° C. and 50° C., respectively) on Brookfield Viscosimeter RVT with Helipath Stand, 2.5 rpm by using the following spindles:
Toothpaste stored at 25° C.: Spindle T-D
Toothpaste stored at 50° C. Spindle T-E
13. Both the pointer and the zero-point were placed in the middle of the window on the Brooktleid and the spindle placed just below the surface. The Brookfield and Helipath stand were started just after the spindle has run 3 times.
14. Three readings were taken for each measurement, and the relative Brookfield units were the average readings multiplied by the following spindle factors:
Factor Spindle T-D=8
Factor Spindle T-E=20
15. After 7 days' storage, the second beaker was transferred from the high-temperature incubator to a 25° C. water bath and kept there for 1 hour.
16. The two 7-days viscosities were measured at 25° C. (after storage at 25° C. and 50° C., respectively) and the relative Brookfield units were calculated as described In step 12.

EXAMPLES

The invention will now be described in more detail with respect to the following non-limiting examples which were performed with the above described equipment, materials and methods.

The following Examples with data set forth in tables 1-8 relate to results obtained by treating the red seaweed *Eucheuma spinosum* with an alkali according to the present invention. The results obtained from the present invention were compared with comparative, prior art neutral extractions, in which the washed seaweed was extracted in demineralized water for one hour at 90° C.

$T_G$ and $T_M$ stand for gelling temperature and melting temperature, respectively, while $T_D$ is the dissolution temperature, and $\eta$ stands for intrinsic viscosity at 60° C. The "% yield" is calculated as: % yield=(g. dry precipitate×1.500×100)/(g. seaweed×g. precipitated extract×seaweed dry matter). Since yield of polymer from seaweed changes with season and with seaweed harvesting location, the yield of neutral extractions of seaweed have been assigned an index of 100, and subsequent calculations of yield index utilize that baseline figure.

The results for the neutral, prior art, extraction were as follows:

TABLE 1

| Extraction | Seaweed g | Amount precipitated g | Precipitate g | Yield % | Yield Index | Na Mg/g | K Mg/g | Ca Mg/g | Mg Mg/g | Cl⁻ % | pH of extract | $T_G$ °C. | $T_M$ °C. | $T_D$ °C. | $\eta$ cP |
|---|---|---|---|---|---|---|---|---|---|---|---|---|---|---|---|
| Neutral | 40.10 | 648.34 | 2.43 | 62.28 | 100 | 26.69 | 38.90 | 6.00 | 7.71 | 0.0 | 9.05 | 25 | 36 | 43 | 300 |

Effect of washing temperature. The process of the present invention involves the treatment of seaweed with salts and/or an alkali, and thus, the new process involves a washing step subsequent to the treatment with salts and/or alkali. This washing is done in order to prevent residues of salts and alkalis In the final extract. Accordingly, in this example, after treatment with salts and/or alkali, the seaweed was washed 4 times for a period of 30 minutes with demineralized water at various temperatures. The seaweed was treated with different concentrations of sodium hydroxide for 2 hours at 5° C.: The results are set forth in Table 2 and shown graphically in FIG. 1.

TABLE 2

| NaOH % | Wash hours | Wash °C. | Seaweed, g | Amount Precipitated g. | Precipitate g | Yield % | Yield Index | $T_G$ °C. | $T_M$ °C. | $T_D$ °C. | Na Mg/g | K Mg/g | Ca Mg/g | Mg Mg/g |
|---|---|---|---|---|---|---|---|---|---|---|---|---|---|---|
| 0 | 2 | 5 | 40.10 | 648.34 | 2.43 | 62.28 | 80 | 24 | 37 | 43 | 26.69 | 38.90 | 6.00 | 7.71 |
| 0 | 2 | 10 | 40.21 | 848.24 | 2.43 | 47.48 | 61 | 32 | 42 | 48 | 25.69 | 39.64 | 6.74 | 8.23 |
| 0 | 2 | 25 | 40.50 | 781.70 | 1.39 | 29.26 | 37 | 37 | 47 | 52 | 25.22 | 33.30 | 8.26 | 8.94 |
| 3 | 2 | 5 | 40.51 | 736.70 | 1.79 | 39.97 | 51 | 14 | 26 | 31 | 65.81 | 2.48 | 3.52 | 2.63 |
| 3 | 2 | 10 | 39.54 | 723.22 | 1.57 | 36.59 | 47 | 13 | 23 | 28 | 65.05 | 2.41 | 3.75 | 2.97 |
| 3 | 2 | 25 | 35.58 | 725.54 | 1.05 | 27.10 | 35 | 17 | 28 | 34 | 63.00 | 1.67 | 4.49 | 3.38 |
| 15 | 2 | 5 | 35.57 | 678.52 | 0.82 | 22.64 | 29 | 13 | 23 | 27 | 67.14 | 0.34 | 4.80 | 2.14 |
| 15 | 2 | 10 | 35.02 | 691.38 | 0.55 | 15.14 | 19 | 12 | 22 | 27 | 62.98 | 0.31 | 5.11 | 2.38 |
| 15 | 2 | 25 | 35.49 | 739.50 | 0.12 | 3.05 | 4 | | | | 54.10 | 0.30 | 5.53 | 2.72 |
| 30 | 2 | 5 | 34.15 | 680.22 | 0.75 | 21.51 | 28 | 14 | 26 | 31 | 64.78 | 0.52 | 4.69 | 1.93 |
| 30 | 2 | 10 | 35.24 | 747.44 | 0.68 | 17.20 | 22 | 14 | 26 | 32 | 63.58 | 0.52 | 4.55 | 2.21 |
| 30 | 2 | 25 | 40.67 | 781.02 | 0.31 | 6.50 | 8 | | | | 58.02 | 0.23 | 5.00 | 3.08 |

(In Table 2, % NaOH = g NaOH/100 ml demineralised water)

As can be seen in Table 2 and FIG. 1, the yield decreases rapidly with increasing washing temperature above 5° C.; and additionally the yield decreases as the concentration of alkali is increased. Thus, in the case of zero concentration of alkali, even though the temperature is below the gelling temperature, the carrageenan polymer contained in *Eucheuma spinosum* will leach out of the seaweed. Furthermore, as alkali is added, the gelling and melting temperatures decrease up to an alkali concentration as high as 15%, which accelerates the leaching of polymer from the seaweed. A possible cause for the increased leaching is the cation composition of the extract. Indeed in table 2 it can be seen that as the alkali concentration increases to about 15%, the level of potassium in the polymer is dramatically decreased, which results in an increase in the solubility of the polymer.

These results indicate that regardless of the alkali concentration, the washing temperature should be held as low as possible, preferably at about 5° C. or lower.

Table 2 and FIG. 2 show the effect on gelling temperature and melting temperature of washing temperature and alkali treatment concentration. As can be seen in Table 2 and FIG. 2 by treating the seaweed with sodium hydroxide, the gelling and melting temperatures are decreased when compared to seaweed, which has not been treated with the alkali. This decrease is observed at sodium hydroxide concentrations as low as 3% and appears to reach the lowest points with about 15% of the alkali. Additionally, FIG. 2 shows that the gelling and melting temperatures increase as the wash temperature increases. Table 2 also shows that the content of potassium ions in the polymer is much lower when the seaweed has been treated with alkali concentration above about 15%, which indicated an increased solubility of the carrageenan polymer since those parts of the polymer which have seen more potassium cations exchanged with monovalent ions would be more soluble and thus, lost during wash at higher temperatures. Finally, it appears that with an alkali treatment, the gelling and melting temperatures remain fairly constant up to a wash temperature of about 10° C.

Effect of the number of washing step. The next step was to look at the number of washing steps. Each washing step took 15 minutes and was performed at 5° C., and the seaweed was treated with 15% and 3% sodium hydroxide for 2 hours at 5° C.:

A selection of the results from Table 3 are shown graphically in FIG. 3. As can be seen, the yield decreases with the number of washing steps. This is particularly true when the concentration of the alkali in the treatment solution is 15%. Again, and without being limited by theory, there seems to be a correlation between the level of potassium in the polymer and the decrease in yield: with higher alkali concentration, the level of potassium in the polymer is lower, and thus the polymer is more water soluble and more likely to leach out of the seaweed and into water.

In table 3, the pH of the extract is indicia of the excess of alkali, and at least one washing step seems to be adequate in order to remove excess alkali. The yields at or above 100% for the zero washing are believed to be caused by alkali being co-precipitated with the carrageenan polymer.

FIG. 4 plots additional results showing the effect of the number of washing steps on gelling and melting temperatures. FIG. 4 shows that gelling temperatures decrease with as many as two washing steps irrespective of alkali concentration, although after two gelling steps the gelling temperatures are slightly increased. The same trend is seen with melting temperatures, although the increase in melting temperature is more pronounced with washing steps above two. Table 3 shows that without washing, both sodium and potassium content of the polymer are high, which reflects a higher residue of sodium hydroxide, which is confirmed by the high pH of the extract.

Without being limited by theory, it is believed that this residue of sodium hydroxide in itself reduces the solubility and increases gelling and melting temperatures. Additionally, the higher content of potassium ions in the carrageenan polymer accounts for at least some of the increased gelling and melting temperatures. As the number of washing steps is increased, the content of potassium ions in the polymer is reduced, and correspondingly the pH of the extract is reduced, which explains the proportional drop in gelling and melting temperatures with increasing number of washing steps. However, the measured concentration of cations may be somewhat misleading, because the concentration is averaged over the entire polymer. But it is strongly believed that the cation

TABLE 3

| NaOH % | Wash No, | Wash °C. | Seaweed g | Amount Precipitated g. | Precipitate g | Yield % | Yield Index | $T_G$ °C. | $T_M$ °C. | $T_D$ °C. | Na Mg/g | K Mg/g | Ca Mg/g | Mg Mg/g | pH of extract |
|---|---|---|---|---|---|---|---|---|---|---|---|---|---|---|---|
| 15 | 1 | 5 | 40.70 | 636.20 | 2.41 | 67.87 | 109 | 12 | 17 | 22 | 79.80 | 0.80 | 0.84 | 0.51 | 9.72 |
| 15 | 2 | 5 | 41.75 | 668.72 | 1.68 | 43.88 | 70 | 10 | 16 | 22 | 74.10 | 0.53 | 3.32 | 1.10 | 8.06 |
| 15 | 3 | 5 | 41.42 | 740.16 | 1.19 | 28.31 | 45 | 12 | 24 | 30 | 68.50 | 0.54 | 4.33 | 1.96 | 7.82 |
| 15 | 4 | 5 | 40.44 | 673.34 | 0.97 | 25.98 | 42 | 12 | 23 | 29 | 65.80 | 0.42 | 4.46 | 2.41 | 7.78 |
| 15 | 0 | 5 | 41.33 | 715.94 | 2.53 | 62.35 | 100 | 20 | 26 | 32 | 104.80 | 1.58 | 0.50 | 0.25 | 12.63 |
| 3 | 1 | 5 | 40.16 | 733.3 | 1.75 | 45.22 | 73 | 7 | 16 | 23 | 73.30 | 2.38 | 2.74 | 1.42 | 9.23 |
| 3 | 2 | 5 | 44.62 | 562.6 | 1.52 | 46.08 | 74 | 9 | 17 | 23 | 71.70 | 2.34 | 3.61 | 1.89 | 8.78 |
| 3 | 3 | 5 | 37.67 | 591.58 | 1.23 | 42.00 | 67 | 11 | 21 | 27 | 68.10 | 1.83 | 3.94 | 2.16 | 8.08 |
| 3 | 4 | 5 | 38.65 | 589.35 | 1.53 | 51.12 | 82 | 11 | 21 | 26 | 67.50 | 1.87 | 4.01 | 2.44 | 8.17 |
| 3 | 0 | 5 | 37.34 | 865.9 | 3.06 | 72.03 | 116 | 10 | 15 | 20 | 80.50 | 4.53 | 0.46 | 0.44 | 10.53 |

(In Table 2, % NaOH = g NaOH/100 ml demineralised water)

concentration is not homogeneous throughout, but instead that different, fractions of the polymer molecule have been subjected to different, levels of ion-exchange between potassium cations and monovalent cations like sodium, with some monovalent-rich fractions reflecting a high amount of ion-exchange activity. This heterogeneity is believed to explain why the gelling and melting temperatures increase with further washing steps because further washing eliminates the monovalent-rich portions (i.e., those subjected to greater ion exchange) more readily than further washing eliminates the potassium-rich portions (i.e., those subjected to less ion exchange).

Effect of alcohol concentration in the wash. Alcohol will prevent the polymer in the seaweed from dissolving, and the next step was to look at washing the treated seaweed in different concentrations of alcohol in demineralized water. The seaweed was treated with 15% sodium hydroxide for 2 hours at 5° C. before washing 4 times 15 minutes in ethanol and water:

thoroughly ion-exchanged fractions of the carrageen polymer are being lost, whereas at higher ethanol concentrations, all of the ion-exchanged polymer fraction are kept relatively water insoluble by the alcohol.

Effect of alkali treatment time. The next experiment looked at the yield index as a function of alkali treatment time. The seaweed was treated at 25° C. and 5° C. for 2 hours, and subsequently washed at 25° C. and at 5° C. with a mixture of 300 ml ethanol and 200 ml demineralized water. G' is the elastic modulus, which indicates the stiffness of the gel and which is measured during the cooling sweep at the point where the elastic modulus, G' intersects with the viscous modulus, G". For comparison, a neutral extraction provides a polymer having G' of about 4.5 Pa.

TABLE 4

| EtOH ml. | Water ml. | Wash °C. | Seaweed g | Amount Precipitated g. | Precipitate g | Yield % | Yield Index | $T_G$ °C. | $T_M$ °C. | $T_D$ °C. | Na Mg/g | K Mg/g | Ca Mg/g | Mg Mg/g | pH of extract |
|---|---|---|---|---|---|---|---|---|---|---|---|---|---|---|---|
| 0 | 1000 | 5 | 40.18 | 704.98 | 1.38 | 35.53 | 57 | 14 | 26 | 31 | 70.00 | 0.44 | 4.40 | 2.20 | 8.93 |
| 100 | 900 | 5 | 40.15 | 680.02 | 1.60 | 42.73 | 69 | 14 | 26 | 32 | 71.60 | 0.34 | 4.10 | 1.90 | 8.83 |
| 300 | 700 | 5 | 40.31 | 724.64 | 1.86 | 46.43 | 75 | 14 | 24 | 30 | 76.10 | 0.50 | 3.50 | 1.20 | 8.75 |
| 600 | 400 | 5 | 40.84 | 645.94 | 2.30 | 63.58 | 102 | 11 | 18 | 23 | 81.80 | 0.79 | 1.40 | 0.66 | 8.79 |
| 0 | 1000 | 25 | 40.62 | 723.04 | 0.68 | 16.88 | 27 | 16 | 28 | 33 | 63.00 | 0.43 | 4.90 | 3.00 | 8.77 |
| 100 | 900 | 25 | 43.89 | 781.60 | 1.93 | 41.03 | 66 | 18 | 29 | 33 | 70.00 | 0.64 | 4.20 | 2.20 | 8.70 |
| 300 | 700 | 25 | 40.27 | 591.40 | 1.70 | 52.05 | 84 | 15 | 26 | 32 | 71.50 | 0.39 | 4.30 | 1.60 | 8.75 |
| 600 | 400 | 25 | 41.29 | 649.18 | 2.38 | 64.75 | 104 | 12 | 18 | 22 | 76.10 | 0.91 | 2.70 | 0.94 | 8.93 |

A selection of the results tabulated in Table 4, are shown graphically in FIG. 5. As can be seen in FIG. 5, increases in the concentration of alcohol (particularly ethanol, or "EtOH") in the treatment liquid significantly increases the yield. Alcohol concentrations in the range 30-60 vol %, and

TABLE 5

| NaOH % | Temp. °C. | Time Min. | Wash °C. | Yield Index | $T_G$ °C. | $T_M$ °C. | $T_D$ °C. | Na Mg/g | K Mg/g | Ca Mg/g | Mg Mg/g | pH of extract | η cP | G' Pa |
|---|---|---|---|---|---|---|---|---|---|---|---|---|---|---|
| 15 | 25 | 120 | 25 | 46 | 14 | 26 | 31 | 74.40 | 0.52 | 2.86 | 1.01 | 9.06 | 400 | 6.0 |
| 15 | 25 | 320 | 25 | 44 | 26 | 36 | 42 | 73.80 | 0.50 | 2.54 | 1.08 | 8.94 | 300 | 6.5 |
| 15 | 25 | 930 | 25 | 42 | 30 | 38 | 43 | 75.10 | 0.43 | 3.25 | 1.27 | 8.95 | 250 | 7.0 |
| 15 | 5 | 120 | 5 | 63 | 12 | 22 | 27 | 82.30 | 0.78 | 1.07 | 0.77 | 8.74 | 350 | 5.5 |
| 15 | 5 | 225 | 5 | 61 | 12 | 22 | 28 | 80.60 | 0.58 | 1.17 | 0.77 | 8.81 | 400 | 6.0 |
| 15 | 5 | 900 | 5 | 52 | 19 | 32 | 38 | 78.60 | 0.55 | 1.44 | 1.26 | 8.83 | 400 | 6.5 |

(% NaOH = g NaOH/100 ML Demineralised Water)

preferably greater than about 50 vol % are particularly effective.

FIG. 6 plots additional results from Table 4, showing the effect of various mixtures of ethanol and demineralized water on the gelling and melting temperatures. Table 4 shows decreasing levels of both calcium ions and magnesium ions in the polymer as the ethanol concentration is increased, and without wishing to be limited by theory a possible explanation could be that at low concentrations of ethanol, the more A selection of the results tabulated in Table 5, are shown graphically in FIG. 7, which show lower yields for longer treatment with sodium hydroxide, especially at the higher (25° C.) temperature. The loss increases with the treatment temperature and with the treatment time.

FIG. 8 plots additional results from Table 5 showing the effect of alkali treatment time on gelling and melting temperatures. FIG. 8 shows an increase in gelling and melting temperatures as the alkali treatment time increases. With about 15% alkali, the gelling and melting temperatures reach a constant level after about 500 minutes at 25° C., whereas the gelling and melting temperatures continue to increase beyond 900 minutes alkali treatment time at 5° C. Table 5 shows that the stiffness of the gels, G' increases with alkali treatment time. This may explain FIG. 8 in as much as with increasing alkali treatment time, the polymer of the seaweed undergoes an increased alkali modification, which results in gels having higher gelling and melting temperatures.

Effect of other alkali types. The next step was to look at the effect on the yield when using different alkalis during treatment of the seaweed. For this, a new batch of *Eucheuma spinosum* was used. The following results were obtained:

A selection of the results tabulated in Table 8 is shown graphically in FIG. 10. Calcium hydroxide treatment is relatively effective with respect to maintaining the polymer in situ within the seaweed during treatment and subsequent washing. 10% calcium hydroxide tends to produce some loss, whereas 20% calcium hydroxide seems to eliminate the loss, particularly when a treatment time of at least about 200 minutes is used.

FIG. 11 shows gelling and melting temperatures at various treatments with calcium hydroxide. FIG. 11 shows very little change in gelling and melting temperatures as the treatment time with calcium hydroxide is increased. The data indicates that higher concentrations of calcium hydroxide during the treatment of the seaweed lead to lower gelling and melting temperatures.

TABLE 6

| Extraction | Seaweed g | Amount precipitated g | Precipitate g | Yield % | Yield Index | Na Mg/g | K Mg/g | Ca Mg/g | Mg Mg/g | Cl⁻ % | pH of extract | $T_G$ ° C. | $T_M$ ° C. | $T_D$ ° C. | η cP |
|---|---|---|---|---|---|---|---|---|---|---|---|---|---|---|---|
| Neutral | 33.74 | 702.12 | 1.72 | 78.18 | 100 | 29.00 | 43.50 | 6.80 | 6.20 | 0.0 | 9.05 | 24 | 35 | 42 | 200 |

In order to obtain the polymers from these experiments in predominantly sodium-cation form, the seaweed was treated with the alkali at 25° C., and subsequently washed at 25° C. twice with 500 ml. 30% sodium chloride and finally twice with 250 ml methanol in 250 ml demineralised water:

The following Examples relate to results obtained using the red seaweed *Euchema spinosum* and treatment with salt.

A new batch of *Eucheuma spinosum* was used to prepare an additional comparative example representing the prior art:

TABLE 7

| Alkali | % | Seaweed g | Amount Precipitated g. | Precipitate g | Yield % | Yield Index | Na Mg/g | K Mg/g | Ca Mg/g | Mg Mg/g | pH of extract | Cl⁻ % |
|---|---|---|---|---|---|---|---|---|---|---|---|---|
| KOH | 15 | 41.13 | 661.76 | 0.40 | 15.82 | 21 | 68.40 | 0.25 | 5.04 | 2.22 | 9.40 | 0.19 |
| NaOH | 15 | 40.69 | 780.66 | 0.58 | 19.66 | 26 | 67.20 | 0.24 | 4.89 | 3.52 | 9.50 | 0.1 |
| Ca(OH)$_2$ | 15 | 40.16 | 640.56 | 1.73 | 72.42 | 98 | 72.40 | 0.16 | 3.81 | 2.10 | 9.59 | 0.19 |

(% Alkali = g Alkali/100 ML demineralized water)

A selection of the results tabulated in Tables 6 and 7 are shown graphically in FIG. 9. The results show that that when the seaweed is treated with sodium hydroxide or potassium hydroxide, a substantial loss in yield follows, whereas the yield is close to unaffected, when calcium hydroxide is used for the treatment.

Effect of calcium hydroxide. In order to further evaluate to effect of calcium hydroxide, tests were performed in which the seaweed was treated with various concentrations of calcium hydroxide at 25° C. The treated seaweed was subsequently treated for 2 hours at 25° C. in 1000 ml 30% sodium chloride and finally washed twice with 250 ml methanol in 250 ml demineralized water. The results were as follows:

TABLE 8

| Ca(OH)$_2$ % | Time Min. | Seaweed g | Amount Precipitated g. | Precipitate g | Yield % | Yield Index | $T_G$ ° C. | $T_M$ ° C. | $T_D$ ° C. | Na Mg/g | K Mg/g | Ca Mg/g | Mg Mg/g | pH of extract |
|---|---|---|---|---|---|---|---|---|---|---|---|---|---|---|
| 10 | 120 | 30.55 | 634.94 | 1.31 | 61.92 | 79.20 | 9 | 17 | 22 | 74.40 | 0.18 | 4.64 | 1.97 | 9.23 |
| 10 | 240 | 30.17 | 568.34 | 1.21 | 64.70 | 82.76 | 8 | 16 | 22 | 73.30 | 0.67 | 5.18 | 1.78 | 8.79 |
| 10 | 960 | 29.19 | 661.20 | 1.17 | 55.58 | 71.09 | 10 | 18 | 24 | 73.10 | 0.22 | 4.75 | 1.90 | 8.91 |
| 20 | 120 | 30.08 | 530.80 | 1.14 | 60.51 | 77.40 | 8 | 15 | 20 | 73.60 | 0.24 | 4.52 | 2.19 | 9.73 |
| 20 | 240 | 30.47 | 495.71 | 1.30 | 72.94 | 93.30 | 7 | 16 | 22 | 72.80 | 0.21 | 4.38 | 1.72 | 9.84 |
| 20 | 960 | 30.05 | 640.20 | 1.91 | 84.14 | 107.62 | 8 | 15 | 21 | 73.60 | 0.25 | 3.92 | 2.01 | 9.49 |

(% Ca(OH)$_2$ = g Ca(OH)$_2$/100 ml demineralised water)

TABLE 9

| Extraction | Seaweed g | Amount precipitated g | Precipitate g | Yield % | Yield Index | Na Mg/g | K Mg/g | Ca Mg/g | Mg Mg/g | Cl⁻ % | pH of extract | $T_G$ °C. | $T_M$ °C. | $T_D$ °C. | η cP |
|---|---|---|---|---|---|---|---|---|---|---|---|---|---|---|---|
| Neutral | 32.00 | 600.00 | 1.20 | 74.23 | 100 | 26.71 | 38.50 | 5.80 | 7.50 | 0.0 | 9.10 | 25 | 36 | 41 | 300 |

A first experiment looked at treatment with sodium chloride at various concentrations and times at 25° C. The treated seaweed was subsequently washed twice in 500 ml demineralised water at 5° C.

TABLE 10

| NaCl % | Time Min. | Seaweed g. | Amount precipitated g. | Precipitate g. | Yield % | Yield Index | Na Mg/g | K Mg/g | Ca Mg/g | Mg Mg/g | Cl⁻ % | pH of extract | $T_G$ °C. | $T_M$ °C. | $T_D$ °C. | η cP |
|---|---|---|---|---|---|---|---|---|---|---|---|---|---|---|---|---|
| 5 | 120 | 29.37 | 554.13 | 0.90 | 46.86 | 63 | 73.00 | 0.38 | 5.46 | 0.89 | 0.0 | 8.25 | 12 | 23 | 29 | 600 |
| 5 | 240 | 28.44 | 562.72 | 1.18 | 62.49 | 84 | 72.30 | 0.55 | 4.95 | 0.84 | 0.0 | 8.18 | 13 | 23 | 28 | 600 |
| 5 | 1020 | 32.90 | 639.84 | 0.89 | 35.83 | 48 | 72.90 | 0.57 | 5.42 | 0.90 | 0.0 | 8.17 | 12 | 22 | 28 | 500 |
| 10 | 150 | 30.11 | 605.00 | 0.52 | 33.90 | 46 | 72.90 | 0.32 | 5.74 | 0.81 | 0.02 | 8.08 | 8 | 15 | 20 | 300 |
| 10 | 240 | 30.38 | 728.94 | 0.49 | 26.28 | 35 | 72.00 | 0.30 | 5.58 | 0.86 | 0.03 | 8.07 | 9 | 16 | 22 | 500 |
| 10 | 1005 | 31.30 | 565.09 | 0.98 | 65.80 | 89 | 73.70 | 0.34 | 4.88 | 0.73 | 0.13 | 8.18 | 13 | 24 | 30 | 600 |
| 20 | 120 | 30.01 | 604.30 | 1.21 | 79.24 | 107 | 73.60 | 0.30 | 4.50 | 0.80 | 0.02 | 7.91 | 9 | 18 | 24 | 500 |
| 20 | 240 | 30.87 | 589.14 | 0.99 | 64.65 | 87 | 72.20 | 0.50 | 4.80 | 0.90 | 0.02 | 8.07 | 10 | 19 | 24 | 500 |
| 20 | 1095 | 30.52 | 601.66 | 1.07 | 69.20 | 93 | 73.60 | 0.30 | 5.00 | 0.80 | 0.02 | 7.96 | 11 | 19 | 25 | 500 |

(% NaCl = g NaCl/100 ml demineralised water.)

A selection of the results tabulated in Table 10 is shown graphically in FIG. 12: with 5% sodium chloride, the yield index starts to fall after a treatment time of about 200 minutes. As the sodium chloride concentration is increased up to about 20%, the yield index increases with increasing treatment time. The optimum appears to be a treatment with 20% sodium chloride for at least about 200 minutes.

FIG. 13 plots additional results from Table 10 and shows that gelling and melting temperatures in general are lower with higher concentrations of sodium chloride during seaweed treatment. Although there is a tendency for increasing gelling and melting temperatures with increasing treatment times at 10% sodium chloride, it seems that gelling and melting temperatures are unaffected by treatment time. Thus, the ion exchange of the polymer in the seaweed appears to take place rapidly within the first about 2 hours of treatment.

Effect of other salts. The Next step was to evaluate the effect of other salts, where seaweed was treated for two hours with a 10% solution of the salt at 25° C. The treated seaweed was subsequently washed twice in a mixture of 500 ml ethanol and 500 ml demineralized water at 50° C.

A selection of the results tabulated in Table 10 is shown graphically in FIG. 14. Together with an alcohol wash, sodium salts of sulphate, phosphate, tri poly phosphate and hexa meta phosphate are as effective to maintain the polymer inside the seaweed as sodium chloride. FIG. 15 shows the effect on gelling and melting temperatures of other salts, and in particular that sodium salts of sulphate, phosphate, poly phosphates and hexa meta phosphate are at least as effective as sodium chloride.

Effect of treatment with alkali and salt. The effect of using both an alkali and a salt was then studied by first treating seaweed with 15% alkali for 73 hours at 5° C., and then washed twice for 15 minutes in 30% sodium chloride solution at 25° C. The treated and washed seaweed was then treated for 4 hours at 25° C. with a 30% sodium chloride solution and finally washed twice with a mixture of 250 ml methanol and 250 ml demineralized water at 25° C.

TABLE 11

| Salt | Time Min. | Yield Index | Na Mg/g | K Mg/g | Ca Mg/g | Mg Mg/g | Cl⁻ % | pH of extract | $T_G$ °C. | $T_M$ °C. | $T_D$ °C. | η cP |
|---|---|---|---|---|---|---|---|---|---|---|---|---|
| Na₂SO₄ | 120 | 95 | 78.60 | 1.66 | 2.65 | 0.43 | 0.0 | 8.01 | 5 | 13 | 18 | 200 |
| Na₃PO₄ × 12H₂O | 120 | 95 | 80.70 | 2.30 | 0.55 | 0.19 | 0.0 | 10.23 | 3 | 15 | 20 | 200 |
| STPP | 120 | 100 | 101.20 | 3.30 | 5.20 | 0.89 | 0.0 | 9.39 | 2 | 14 | 20 | 90 |
| Na-Hexa | 120 | 96 | 86.60 | 1.40 | 6.60 | 1.10 | 0.0 | 8.84 | 0 | 13 | 19 | 90 |

(% SALT = g SALT/100 ml demineralised water.)

TABLE 12

| Alkali | % | Seaweed g. | Amount precipitated g. | Precipitate g. | Yield % | Yield Index | Na Mg/g | K Mg/g | Ca Mg/g | Mg Mg/g | Cl- % | pH of extract |
|---|---|---|---|---|---|---|---|---|---|---|---|---|
| KOH | 15 | 41.13 | 661.76 | 0.40 | 15.82 | 21 | 68.40 | 0.25 | 5.04 | 2.22 | 0.19 | 9.40 |
| NaOH | 15 | 40.69 | 780.66 | 0.58 | 19.66 | 26 | 67.20 | 0.24 | 4.89 | 3.52 | 0.10 | 9.50 |
| Ca(OH)$_2$ | 15 | 40.16 | 640.56 | 1.73 | 72.42 | 99 | 72.40 | 0.16 | 3.81 | 2.10 | 0.19 | 9.59 |

(% ALKALI = g ALKALI/100 ml demineralised water)

A selection of the results tabulated in Table 12 is shown graphically in FIG. 16 and show that yield decreases when salt is used for treatment subsequent to treatment with sodium hydroxide and potassium hydroxide. However, the yield is maintained when the alkali treatment is performed with calcium hydroxide.

The following were examples and experiments, the results of which are set forth in Tables 13-14, were performed in order to provide a means for maintaining the yield when using sodium hydroxide as the alkali before treatment with sodium chloride The process involved the following steps: the washed seaweed was treated with 20% sodium hydroxide in the water phase and varying quantities of ethanol for 3 hours at 5° C. The treated seaweed was then washed once in 30% sodium chloride solution at 5° C. and treated with a 20% sodium chloride solution for 2 hours at 5° C. The seaweed was then washed twice in a mixture of 600 ml ethanol and 400 ml demineralized water at 5° C. before being extracted in demineralized water at 90° C. for 1 hour, filtered and precipitated in three volumes of 100% isopropyt alcohol, dried and milled.

Effect of alcohol during alkali treatment. As comparison, one test was done using a mixture of 600 ml ethanol and 400 ml demineralized water instead of a 30% sodium chloride solution during the wash after alkali treatment.

treatment, the yield can be preserved The amount of ethanol should be at least 100 ml ethanol per liter and preferably above about 200 ml ethanol per liter. Table 13 further shows that using ethanol during the first wash is as effective in preserving the yield as sodium chloride is.

FIG. 18 plots additional results from Table 13 and shows that melting and gelling temperatures stay largely unaffected by the use of ethanol during alkali treatment. The fluctuation is attributed to experimental uncertainty.

Effect of temperature during alkali treatment. In further experiments, the effect of temperature during alkali treatment was evaluated. The process was the same as the process used for the data in Table 13, using salt in the first wash, but while varying the temperature during alkali treatment.

TABLE 13

| % NaOH | Time hours | ml EtOH per l. | First wash | Yield Index | Na Mg/g | K Mg/g | Ca Mg/g | Mg Mg/g | $T_G$ °C. | $T_M$ °C. | $T_D$ °C. | η cP | pH of extract |
|---|---|---|---|---|---|---|---|---|---|---|---|---|---|
| 20 | 3 | 0 | EtOH | 68 | 69.50 | 0.26 | 2.50 | 1.10 | 5 | 15 | 20 | 200 | 8.21 |
| 20 | 3 | 0 | NaCl | 70 | 68.80 | 0.31 | 1.90 | 0.85 | 7 | 16 | 22 | 250 | 8.18 |
| 20 | 3 | 100 | NaCl | 82 | 69.50 | 0.35 | 1.60 | 0.83 | 6 | 16 | 21 | 200 | 8.64 |
| 20 | 3 | 250 | NaCl | 94 | 69.50 | 0.74 | 1.70 | 1.20 | 8 | 17 | 23 | 250 | 8.58 |
| 20 | 3 | 400 | NaCl | 98 | 70.20 | 0.78 | 1.70 | 1.40 | 8 | 18 | 25 | 250 | 8.61 |
| 20 | 3 | 500 | NaCl | 99 | 70.10 | 0.43 | 1.90 | 1.40 | 4 | 15 | 21 | 250 | 8.63 |
| 20 | 3 | 600 | NaCl | 98 | 69.20 | 0.32 | 1.90 | 2.10 | 9 | 17 | 23 | 300 | 8.52 |

A selection of the results tabulated in Table 13 is shown graphically in FIG. 17. By using ethanol during the alkali

TABLE 14

| ml EtOH per l | Temp. °C. | Yield Index | Na Mg/g | K Mg/g | Ca Mg/g | Mg Mg/g | $T_G$ °C. | $T_M$ °C. | $T_D$ °C. | η cP | pH of extract |
|---|---|---|---|---|---|---|---|---|---|---|---|
| 600 | 5 | 98 | 69.20 | 0.32 | 1.90 | 2.10 | 9 | 17 | 22 | 300 | 8.52 |
| 600 | 25 | 98 | 72.70 | 0.19 | 1.80 | 1.76 | 20 | 31 | 37 | 300 | 9.70 |
| 600 | 35 | 101 | 71.90 | 0.36 | 2.20 | 1.67 | 26 | 36 | 43 | 300 | 9.50 |
| 600 | 50 | 102 | 70.40 | 0.52 | 2.20 | 1.82 | 27 | 36 | 42 | 200 | 9.08 |
| 600 | 70 | 80 | 70.20 | 0.50 | 2.10 | 1.80 | 24 | 33 | 39 | 100 | 9.68 |
| 400 | 5 | 98 | 70.20 | 0.78 | 1.70 | 1.40 | 8 | 18 | 24 | 250 | 8.61 |
| 400 | 25 | 109 | 71.10 | 0.36 | 2.00 | 1.90 | 22 | 33 | 38 | 300 | 9.71 |
| 400 | 35 | 99 | 71.30 | 0.32 | 1.90 | 1.58 | 27 | 36 | 42 | 300 | 9.73 |
| 400 | 50 | 103 | 71.20 | 0.27 | 1.70 | 1.45 | 25 | 35 | 40 | 200 | 9.80 |
| 400 | 70 | 83 | 71.25 | 0.25 | 1.65 | 1.40 | 26 | 35 | 41 | 100 | 9.57 |
| 200 | 25 | 89 | 74.82 | 0.26 | 1.72 | 1.22 | 17 | 28 | 34 | 200 | 9.50 |
| 200 | 35 | 92 | 74.50 | 0.20 | 1.69 | 1.12 | 26 | 35 | 41 | 200 | 9.64 |
| 200 | 50 | 75 | 72.80 | 0.28 | 2.10 | 1.36 | 26 | 35 | 40 | 200 | 8.90 |

TABLE 14-continued

| ml EtOH per l | Temp. °C. | Yield Index | Na Mg/g | K Mg/g | Ca Mg/g | Mg Mg/g | $T_G$ °C. | $T_M$ °C. | $T_D$ °C. | η cP | pH of extract |
|---|---|---|---|---|---|---|---|---|---|---|---|
| 100 | 5  | 82 | 69.50 | 0.35 | 1.60 | 0.83 | 6  | 16 | 22 | 200 | 8.64 |
| 100 | 25 | 88 | 75.46 | 0.25 | 1.59 | 1.14 | 19 | 29 | 34 | 250 | 9.69 |
| 100 | 35 | 86 | 75.21 | 0.28 | 1.57 | 1.21 | 26 | 35 | 40 | 200 | 9.60 |
| 100 | 50 | 77 | 74.46 | 0.64 | 1.85 | 1.18 | 35 | 45 | 51 | 100 | 9.18 |

A selection of the results tabulated in Table 14 is shown graphically in FIG. 19. With alkali treatment temperatures up to about 40° C., yield is largely maintained as long as the ethanol concentration during alkali treatment is at least 100 ml. ethanol per liter. However, as the temperature is increased to about 40-about 60° C., the ethanol concentration should be increased to about 400-about 600 ml ethanol per liter. As the temperature increases further, the yield appears to drop. It is speculated, that this drop in yield is actually caused by the polymer in the seaweed becoming increasingly insoluble as a result of the treatment with the alkali, which at the higher temperatures accelerates the modification of the polymer in situ, thus, making the polymer less soluble. A higher temperature during extraction is believed to increase the yield.

FIG. 20 plots additional results from Table 14 and shows that melting and gelling temperatures can be controlled through the alkali treatment temperature, but also through the concentration of ethanol during the alkali treatment. Thus, for all concentrations of ethanol, gelling and melting temperatures are increased the same up to an alkali treatment temperature of about 30-35° C. When the ethanol concentration is higher than about 200 ml. ethanol per liter, the gelling and melting temperatures remain constant, whereas these continue to increase with concentrations of ethanol during treatment of about 100 ml. ethanol per liter.

With ethanol concentrations in the range from about 200 ml. ethanol per liter to about 600 ml. ethanol per liter, the gelling temperature can be controlled in the range from about 6° C. to about 27° C. Similarly, the melting temperature can be controlled in the range from about 16° C. to about 36° C. This by varying the treatment temperature within the range from about 5° C. to about 35° C.

However, when using lower concentrations of ethanol during the alkali treatment, the gelling and melting temperatures can be controlled in a wider range. The gelling temperature can be controlled in the range from about 6° C. to about at least 35° C., Similarly, the melting temperature can be controlled in the range from about 16° C. to about at least 45° C. This by varying the treatment temperature from about 5° C. to about at least 50° C.

Water-in-oil emulsions. In this example, water-in-oil emulsions were made without salt and with salt. The salt in the form of sodium chloride was used to simulate a margarine and to show that the carrageenan products of the present invention can be used in margarine products as well as in other water-in-oil emulsions containing salt.

First, carrageenan was manufactured in the following steps for use in the water-in-oil emulsion. Washed seaweed was treated with 20% sodium hydroxide in the water phase and 60 vol % of ethanol for 3 hours at 5° C. The treated seaweed was then washed once in 30% sodium chloride solution at 5° C. and treated with a 20% sodium chloride solution for 2 hours at 5° C. The seaweed was then washed twice in a mixture of 600 ml ethanol and 400 ml demineralized water at 25° C. before being extracted in demineralized water at 90° C. for 1 hour, filtered and precipitated in three volumes of 100% isopropyl alcohol, dried and milled.

A water-in-oil emulsion, which is solid below a certain temperature but liquid at higher temperatures can be made without the use of emulsifiers and since the continuous phase is composed of oil, the water-in-oil emulsion can be formulated without the use of preservatives.

In order to make an oil phase, which melts at different temperatures, iso propyl palmitate and bees wax were mixed in different proportions, heated to 75° C., and cooled in a refrigerator. Afterward, the solid fat was slowly heated and the temperature recorded when the solid became liquid and easy to stir.

TABLE 15

| IPP % | B-wax % | Liquid OC |
|---|---|---|
| 87.5 | 12.5 | 24 |
| 75 | 25 | 43 |
| 50 | 50 | 50 |
| 25 | 75 | 57 |

Thus, a liquefying temperature of about 35° C. is achieved with a mix of 82% iso propyl palmitate and 18% bees wax.

Such an oil blend was used together with the carrageenan manufactured for use in the water-in-oil emulsion, as discussed above.

The water-in-oil emulsion was made by first heating 25 g of the blend of oils to 75° C. and cooling it to 55° C. Similarly, the carrageenan of the present invention was dispersed in 25 g of cold demineralized water and stirred until fully dissolved. The carrageenan solution was then heated to 55° C., and slowly added to the 55° C. hot oil blend while emulsifying using a high speed mixer—Heidolph SilentCrusher M—running at a speed of about 10,000 rpm. When the emulsion was made, the emulsion was cooled on a 5° C. with slow stirring to about 35-40° C. The emulsion was lastly placed in a refrigerator at 5° C. C over night.

This experiment was repeated with the addition of pectin. The pectin was dissolved and heated together with the carrageenan product of the present invention to utilize the pH reducing effect of pectin as disclosed in PCT Patent Publication Mo. WO/2005102262. The pectin had a degree of esterification of 73.2% and the pH of the pectin was adjusted to about 5.5.

The samples were evaluated visually for phase separation and they were evaluated when spread on the skin. The results are set forth in Table 16, below.

TABLE 16

| "Alkali and Salt", % in water phase | NaCl % In water phase | Pectin % In water phase | Stability, 14 days 25° C. | Skin feel |
|---|---|---|---|---|
| 0.00 | 0 | 0 | Separation | Oily |
| 0.20 | 0 | 0 | Stable | Slightly oily |
| 0.40 | 0 | 0 | Stable | Non-oily - good spread |
| 0.80 | 0 | 0 | Stable | Non-oily - like an O/W - very good spread |
| 1.60 | 0 | 0 | Stable | Non-oily - like an O/W - excellent spread |
| 0.08 | 3 | 0 | Separation | Oily |
| 0.16 | 3 | 0 | Stable | Non-oily - Good spread |
| 0.32 | 3 | 0 | Stable | Non-oily - like an O/W - very good spread |
| 0.08 | 2 | 0 | Stable | Oily |
| 0.16 | 2 | 0 | Stable | Non-oily - like an O/W - very good spread |
| 0.32 | 2 | 0 | Stable | Non-oily - like an O/W - very good spread |
| 0.12 | 1 | 0 | Stable | Oily |
| 0.24 | 1 | 0 | Stable | Non-oily - like an O/W - very good spread |
| 0.48 | 1 | 0 | Stable | Non-oily - like an O/W - very good spread |
| 0.80 | 0 | 1 | Stable | Non-oily - like an O/W - very good spread |

Without salt, the carrageenan products of the present invention provide stable and spreadable water-in-oil emulsions at body temperature. The concentration of carrageenan in the water phase is optimal in the range from about 0.40% to at least 1.60%.

With salt, the carrageenan products of the present invention also provide for stable water-in-oil emulsions, which liquefy at body temperature. The concentration of carrageenan in the water phase is optimal in the range from about 0.16 to at least 0.48%.

The carrageenan products of the present invention provide for stable water-in-oil emulsions in the presence of pectin, which liquefy on the skin. Thus, the carrageenan products of the present invention can be used to form emulsifier-free and preservative-free water-in-oil emulsions, which appear to invert into oil-in-water when spread on the skin's surface. In addition, these emulsions can be made to be pH-reducing. A personal care product prepared according to the present invention can, for example, be in the form of a water-in-oil emulsion comprising 20-80% oil, and where said emulsion inverts at any temperature in the range 15-45° C., preferably 30-35° C. to ensure inversion on the skin surface.

Additionally, by changing the ratio of oil and wax or by using another blend of oils and fats, an oil blend can be made, which melts in the mouth and thus, water-in-oil emulsions can be made with carrageenan products of the present invention, which invert in the mouth to oil-in-water emulsions to release aromas and salt in the mouth.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

I claim:

1. An iota carrageenan composition comprising:
    sodium in the range of about 5.410 wt % to about 8.230 wt %;
    potassium in the range of about 0.023 wt % to about 0.248 wt %,
    calcium in the range of about 0.046 wt % to about 0.553 wt %; and
    magnesium in the range of about 0.051 wt % to about 0.338 wt %;
    wherein the iota carrageenan composition has a gelling temperature in the range of about 7° C. to about 30° C. and a melting temperature in the range of about 16° C. to about 38° C.

2. A food product comprising the iota carrageenan composition according to claim 1.

3. The food product according to claim 2, wherein the food product is selected from the group consisting of processed meat, poultry, and fish.

4. The food product according to claim 2, wherein the food product is an oil-in-water emulsion.

5. The food product according to claim 4, wherein the emulsion is in the form of margarine and comprises about 20 wt % to about 80 wt % fat.

6. An iota carrageenan composition comprising
    sodium in the range of about 7.200 wt % to about 10.120 wt %;
    potassium in the range of about 0.030 wt % to about 0.330 wt %;
    calcium in the range of about 0.055 wt % to about 0.574 wt %; and
    magnesium in the range of about 0.019 wt % to about 0.110 wt %;
    wherein the iota carrageenan composition has a gelling temperature in the range of about 0° C. to about 13° C. and a melting temperature in the range of about 13° C. to about 24° C.

7. A food product comprising the iota carrageenan composition according to claim 6.

8. The food product according to claim 7, wherein the food product is selected from the group consisting of processed meat, poultry, and fish.

9. The food product according to claim 7, wherein the food product is an oil-in-water emulsion.

10. The food product according to claim 9, wherein the emulsion is in the form of margarine and comprises about 20 wt % to about 80 wt % fat.

11. An iota carrageenan composition comprising:
    sodium in the range of about 6.720 wt % to about 7.546 wt %;
    potassium in the range of about 0.017 wt % to about 0.078 wt %;
    calcium in the range of about 0.140 wt % to about 0.250 wt %; and
    magnesium in the range of about 0.083 wt % to about 0.210 wt %;
    wherein the gelling temperature of the iota carrageenan composition is in the range of about 4° C. to about 35° C. and the melting temperature is in the range of about 15° C. to about 45° C.

12. A food product comprising the iota carrageenan composition according to claim 11.

13. The food product according to claim 12, wherein the food product is selected from the group consisting of processed meat, poultry, and fish.

14. The food product according to claim 12, wherein the food product is an oil-in-water emulsion.

15. The food product according to claim 14, wherein the emulsion is in the form of margarine and comprises about 20 wt % to about 80 wt % fat.

16. The iota carrageenan composition according to claim 15, which has the following gelling and melting temperatures when incorporated into demineralised water:

| System | Carrageenan % | $T_G$ ° C. | $T_M$ ° C. |
|---|---|---|---|
| Demineralised water | 0.60 | −15−−10 | −5-0 |
|  | 1.00 | −10−−5 | 0-7 |
|  | 1.50 | −5-6 | 7-15 |

17. The iota carrageenan composition according to claim 11, which has the following gelling and melting temperatures when incorporated into demineralised water and sodium chloride:

| System | Carrageenan % | NaCl % | $T_G$ ° C. | $T_M$ ° C. |
|---|---|---|---|---|
| Demineralised water and NaCl | 0.60 | 1.00 | 45-55 | 50-62 |
|  | 0.60 | 3.00 | 63-75 | 67-85 |
|  | 0.60 | 5.00 | 74-83 | 78-87 |

18. The iota carrageenan composition according to claim 11, which has the following gelling and melting temperatures when incorporated into demineralised water containing potassium chloride:

| Carrageenan % | KCl % | $T_G$ ° C. | $T_M$ ° C. |
|---|---|---|---|
| 1.00 | 0.00 | −10−−5 | 0-7 |
|  | 0.04 | −5-5 | 5-15 |
|  | 0.12 | 0-13 | 10-23 |
|  | 0.16 | 7-18 | 15-28 |
|  | 0.32 | 17-30 | 28-38 |

19. The iota carrageenan composition according to claim 11, which has the following gelling and melting temperatures when incorporated into demineralised water containing calcium chloride:

| Carrageenan % | $CaCl_2 \cdot 2H_2O$ | $T_G$ | $T_M$ |
|---|---|---|---|
| 1.00 | 0.08 | 15-34 | 30-44 |
|  | 0.16 | 42-55 | 52-61 |
|  | 0.32 | 60-74 | 67-83 |

* * * * *